United States Patent
Shiba et al.

(10) Patent No.: US 11,883,100 B2
(45) Date of Patent: Jan. 30, 2024

(54) OPHTHALMOLOGIC IMAGE PROCESSING METHOD AND OCT APPARATUS

(71) Applicant: NIDEK CO., LTD., Aichi (JP)

(72) Inventors: Ryosuke Shiba, Aichi (JP); Yukihiro Higuchi, Aichi (JP); Shinya Iwata, Aichi (JP); Junpei Nishiyama, Aichi (JP); Hideki Aono, Aichi (JP); Hirofumi Yogo, Aichi (JP)

(73) Assignee: NIDEK CO., LTD., Aichi (JP)

( * ) Notice: Subject to any disclaimer, the term of this patent is extended or adjusted under 35 U.S.C. 154(b) by 794 days.

(21) Appl. No.: 17/034,742

(22) Filed: Sep. 28, 2020

(65) Prior Publication Data

US 2021/0093186 A1   Apr. 1, 2021

(30) Foreign Application Priority Data

Sep. 30, 2019 (JP) ................. 2019-180051
Jan. 8, 2020 (JP) ................. 2020-001769
Jan. 8, 2020 (JP) ................. 2020-001770
Jul. 3, 2020 (JP) ................. 2020-116012

(51) Int. Cl.
*A61B 3/10* (2006.01)
*A61B 3/00* (2006.01)
*A61B 3/12* (2006.01)

(52) U.S. Cl.
CPC ............ *A61B 3/102* (2013.01); *A61B 3/0008* (2013.01); *A61B 3/0025* (2013.01); *A61B 3/0041* (2013.01); *A61B 3/12* (2013.01)

(58) Field of Classification Search
CPC ... A61B 3/0008; A61B 3/0025; A61B 3/0041; A61B 3/102; A61B 3/12
See application file for complete search history.

(56) References Cited

U.S. PATENT DOCUMENTS

| | | |
|---|---|---|
| 6,980,299 B1 | 12/2005 | de Boer |
| 2009/0196477 A1 | 8/2009 | Cense et al. |
| 2010/0007848 A1 | 1/2010 | Murata |
| 2010/0014089 A1 | 1/2010 | Yamada et al. |
| 2012/0083667 A1 | 4/2012 | Isogai et al. |

(Continued)

FOREIGN PATENT DOCUMENTS

| | | |
|---|---|---|
| EP | 3 536 222 A2 | 9/2019 |
| JP | 2008-501118 A | 1/2008 |

(Continued)

OTHER PUBLICATIONS

Office Action dated Mar. 22, 2023 by the Japanese Patent Office in counterpart Japanese Patent Application No. 2019-180051.

(Continued)

*Primary Examiner* — Jack Dinh
(74) *Attorney, Agent, or Firm* — Sughrue Mion, PLLC

(57) ABSTRACT

Provided are ophthalmologic image processing method, including an acquisition step of acquiring OCT data of an eye to be examined based on a spectral interference signal output from an OCT optical system, a setting step of setting a depth region including an image position of a tissue as an extraction region for data on one-direction side from a zero delay position in the OCT data, and a display control step of extracting extracted OCT data corresponding to the extraction region from the OCT data and displaying the extracted OCT data in a display region set in advance on a monitor, and an OCT apparatus that executes the method.

15 Claims, 13 Drawing Sheets

(56) References Cited

U.S. PATENT DOCUMENTS

| | | |
|---|---|---|
| 2013/0208240 A1 | 8/2013 | Sharma et al. |
| 2015/0327762 A1 | 11/2015 | Isogai et al. |
| 2017/0211925 A1 | 7/2017 | Kobayashi et al. |
| 2018/0135962 A1 | 5/2018 | Murata et al. |
| 2020/0037872 A1 | 2/2020 | Shiba et al. |

FOREIGN PATENT DOCUMENTS

| | | |
|---|---|---|
| JP | 2010-12111 A | 1/2010 |
| JP | 2010-29648 A | 2/2010 |
| JP | 2012-75640 A | 4/2012 |
| JP | 2015-506772 A | 3/2015 |
| JP | 2016-55122 A | 4/2016 |
| JP | 2018-63193 A | 4/2018 |
| JP | 2019-042249 A | 3/2019 |
| JP | 2019-150409 A | 9/2019 |
| JP | 2020-22723 A | 2/2020 |
| WO | 2016/017664 A1 | 2/2016 |

OTHER PUBLICATIONS

Office Action dated Jul. 11, 2023, issued by Japanese Patent Office in Japanese Patent Application No. 2020-001769.

Wojtkowski, W. et al., "Full range complex spectral optical coherence tomography technique in eye imaging", Optics Letters, Aug. 15, 2002, vol. 27, No. 16, pp. 1415-1417. (3 pages total).

Grulkowski, Ireneusz et al., "High-precision, high-accuracy ultralong-range swept-source optical coherence tomography using vertical cavity surface emitting laser light source", Published in final edited form as: Opt Lett, Mar. 1, 2013, vol. 38, No. 5, pp. 673-675. (9 pages total).

INITIAL POSITION

THIRD POSITION

FOURTH POSITION

OPHTHALMOLOGIC IMAGE PROCESSING METHOD AND OCT APPARATUS

CROSS-REFERENCE TO RELATED APPLICATION

This application claims priority from Japanese Patent Applications No. 2019-180051 filed on Sep. 30, 2019, No. 2020-001769 filed on Jan. 8, 2020, No. 2020-001770 filed on Jan. 8, 2020, and No. 2020-116012 filed on Jul. 3, 2020, the entire subject-matter of which is incorporated herein by reference.

TECHNICAL FIELD

The present disclosure relates to an ophthalmologic image processing method of processing OCT data of a tissue of an eye to be examined and an OCT apparatus for executing the ophthalmologic image processing method.

BACKGROUND

In recent years, in a field of ophthalmology, an optical coherence tomography (OCT), which is an apparatus for capturing a tomographic image of a tissue of an eye to be examined, attracts attention (for example, refer to Japanese Patent Publication No. 2016-55122).

In SD-OCT, which is relatively popular in ophthalmology, an effective imaging range in a depth direction is about 2 mm to 3 mm from an origin position (zero delay position) in OCT data.

On the other hand, various attempts are made to improve a depth of penetration in the OCT data (that is, to expand the imaging range in the depth direction).

It has been reported by Non-Patent Document 1 (Ireneusz Grulkowski. et al. (2013) High-precision, high-accuracy ultralong-range swept-source optical coherence tomography using vertical cavity surface emitting laser light source, Opt Lett. 2013 Mar. 1; 38(5): 673-675) and the like that the imaging range can be significantly improved by improvement of a light source or the like. The Non-Patent Document 1 reports, for example, that employment of a light source called VCSEL, which emits light with a long coherence length, as an OCT light source is effective in improving the depth of penetration.

In a case where the OCT data captured by an apparatus in the related art is displayed, the entire imaging range is displayed as it is (for example, refer to Japanese Patent Publication No. 2016-55122). A range of an image of a subject in the OCT data is drawn in a relatively narrower range as the depth of penetration in the OCT data is higher (the imaging range in the depth direction is wider). Therefore, it is considered that observation of the tissue becomes difficult in a case where a display method similar to that of Japanese Patent Publication No. 2016-55122 is employed.

SUMMARY

An object of the present disclosure is to provide an ophthalmologic image processing method in which at least one of acquisition and display of OCT data with high depth of penetration is performed well and an OCT apparatus that executes the method.

An ophthalmologic image processing method according to the present disclosure is an ophthalmologic image processing method performed by a computer and includes an acquisition step of acquiring OCT data of an eye to be examined generated by an image processor based on a spectral interference signal output from an OCT optical system that detects the spectral interference signal between measurement light guided to a tissue of the eye to be examined and reference light, a setting step of setting a depth region including an image position of the tissue as an extraction region for data on one-direction side from a zero delay position in the OCT data, and a display control step of extracting extracted OCT data corresponding to the extraction region from the OCT data and displaying the extracted OCT data in a display region set in advance on a monitor.

An OCT apparatus according to the present disclosure includes an OCT optical system that detects a spectral interference signal between measurement light guided to a tissue of an eye to be examined and reference light, an image processor that generates OCT data of the eye to be examined based on the spectral interference signal output from the OCT optical system, and a computer that executes the above ophthalmologic image processing method.

DETAILED DESCRIPTION

"Outline"

Figure 1:
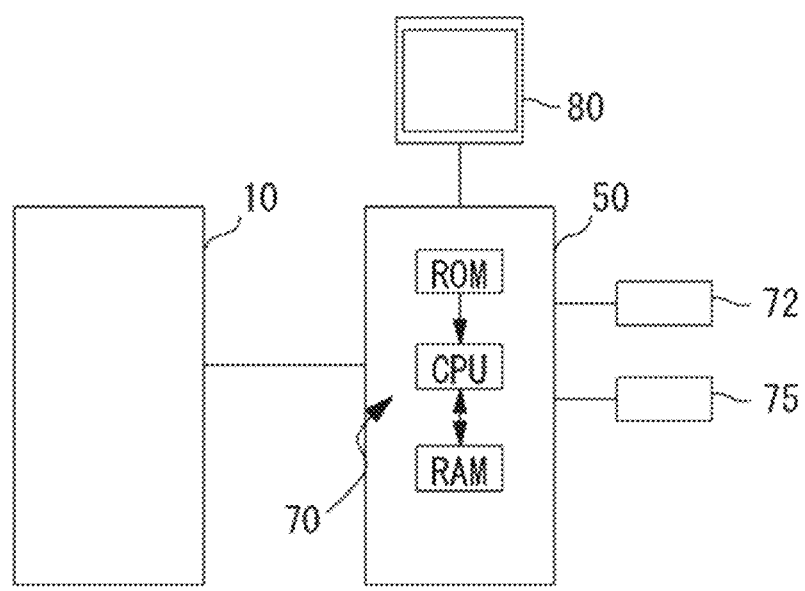
FIG. 1 is a diagram showing a schematic configuration of an OCT system according to an example.

Embodiments of the present disclosure will be described. Items classified by < > below may be used independently or in association with each other. For example, in an embodiment, a plurality of items may be combined as appropriate. For example, an item described in a certain embodiment may be applied to another embodiment.

First Embodiment

First, a first embodiment will be described. An OCT apparatus according to the first embodiment can acquire good OCT data at different sweep frequencies.

<OCT Optical System>

An OCT optical system (refer to FIG. 2) is used to image OCT data of an eye to be examined. The OCT optical system detects a spectral interference signal between measurement light guided to a tissue of the eye to be examined and reference light.

The OCT optical system may be suitable for acquiring the OCT data with high depth of penetration (in other words, wide area). For example, the OCT optical system according to the first embodiment is a wavelength sweep OCT (SS-OCT) optical system. In this case, the OCT optical system includes a wavelength sweep light source (wavelength scanning light source) as an OCT light source, which is a light source for the measurement light and the reference light. The wavelength sweep light source changes an emission wavelength at high speed with time. For example, a VCSEL wavelength sweep light source has a long coherence length. Therefore, the source can be used as the OCT light source to image the wide-area OCT data in the depth direction. For example, an imaging range of about 10 mm or more can be realized. Accordingly, a plurality of tissues at different depth positions in the eye to be examined can be imaged once. As a specific example, both a fundus and a translucent body may be imaged once. It is preferable that the wavelength sweep light source performs wavelength sweep in a so-called 1 μm band (performs wavelength sweep around about 1050 nm). It is known that the so-called 1 μm band shows the high depth of penetration for the tissue of the eye to be examined, as compared with another wavelength band.

The sweep frequency in the wavelength sweep light source according to the first embodiment can be changed at least between a first frequency and a second frequency. The second frequency has a smaller value than the first frequency. For example, any one of a speed or a duty ratio of an optical element which is built in the light source and driven to sweep the wavelength is changed to change the sweep frequency.

The OCT optical system according to the first embodiment includes at least a light splitting unit and a detector. The OCT optical system may additionally include a scanning unit (also referred to as an optical scanner). The light splitting unit splits light from the OCT light source into the measurement light and the reference light. The scanning unit is a device for scanning the measurement light on the tissue of the eye to be examined. The scanning unit may be, for example, a combination of two optical scanners having different scanning directions. The detector receives the measurement light guided to the eye to be examined and the reference light to output the spectral interference signal. The OCT optical system may scan the measurement light along a plurality of scanning lines set in advance on the tissue of the eye to be examined and image the OCT data of each of the plurality of scanning lines. The scanning line may be set at any position based on an instruction from an examiner. Any one of a plurality of scan patterns set in advance may be selected to set a scanning line corresponding to the scan pattern. Various scan patterns such as line, cross, multi, map, radial, and circle are known.

<Conversion Unit>

A conversion unit samples the spectral interference signal output from the detector. The spectral interference signal is detected as a beat signal along with the wavelength sweep. The conversion unit converts the spectral interference signal output from the detector from an analog signal to a digital signal. The conversion unit may be a digitizer capable of adjusting a sampling frequency.

<Image Processor>

The image processor processes the spectral interference signal output from the OCT optical system to acquire the OCT data of the eye to be examined. More specifically, the spectral interference signal converted into the digital signal by the conversion unit is arithmetically processed by the image processor. Accordingly, the OCT data of the eye to be examined is acquired.

<OCT Data>

The OCT data may be signal data or visualized image data. For example, the OCT data may be at least one of tomographic image data indicating reflection intensity characteristics of the eye to be examined, OCT angio data of the eye to be examined (for example, OCT motion contrast data), Doppler OCT data indicating Doppler characteristics of the eye to be examined, and polarization characteristic data indicating polarization characteristics of the eye to be examined.

The OCT data may be at least one of B scan data (for example, B scan tomographic image data, two-dimensional OCT angio data, or the like), enface data (for example, OCT enface data, enface motion contrast data, or the like), and three-dimensional data (for example, three-dimensional tomographic image data, three-dimensional OCT angio data, or the like).

<Application of Full-Ranging Technique>

A full-ranging technique may be applied to the OCT data. Various methods of removing a virtual image in the OCT data are referred to as the full-ranging techniques. In the present embodiment, any one of the full-ranging techniques may be applied. Accordingly, OCT data with a wider range in which the virtual image is selectively removed may be acquired.

Examples of the full-ranging technology include a technique of removing a virtual image (also referred to as a mirror image) by additional hardware (refer to, for example, Non-Patent Document 2: Wojtkowski, M. et al. (2002) Full range complex spectral optical coherence tomography technique in eye imaging, Optics Letters, 27 (16), p. 1415) and technique of performing correction by software without using additional hardware (refer to, for example, Japanese Patent Publication No. 2015-506772).

The application by the present applicant (JP-A-2020-22723) proposes another full-ranging technique in which at least complementary processing is performed on an overlapping region of a real image and a virtual image in the OCT data, based on a plurality of OCT data having different optical path lengths when a spectral interference signal is detected, to generate OCT data subjected to the complementary processing. The technique may be applied to the present embodiment.

<Arithmetic Control Unit>

An arithmetic control unit is a processor that is configured to control an operation of the entire OCT apparatus. The arithmetic control unit may be configured of, for example, a CPU, a RAM, a ROM, and the like. The image processor may be used by the arithmetic control unit.

In the first embodiment, the arithmetic control unit controls the sweep frequency in the wavelength sweep light source. The control unit changes the sweep frequency between at least the first frequency and the second frequency that is smaller than the first frequency. Accordingly, a plurality of conditions in the OCT data may be changed. Examples of the plurality of conditions include an SN ratio of the spectral interference signal, the imaging range in the depth direction, and a correspondence relationship between a sampling timing and a wavelength of light emitted from the light source.

Although the details will be described below in the example, the SN ratio of the spectral interference signal may take a larger value at the second frequency than at the first frequency.

By the way, in the SD-OCT, interference fringes of the measurement light and the reference light are spectrally detected by a spectrometer to detect the spectral interference signal. Therefore, in the SD-OCT, noise in the spectral interference signal can be suppressed by controlling an exposure time of a camera (line sensor). On the other hand, since there is no concept of the exposure time in the SS-OCT, the SD-OCT method cannot be employed. There is a limit from a viewpoint of safety even though an amount of measurement light incident on the eye to be examined is increased to suppress noise. Therefore, in the SS-OCT, the change in the sweep frequency is considered to be significant in adjusting the SN ratio of the spectral interference signal.

In the SS-OCT, in a case where a sampling rate of the spectral interference signal is constant, the imaging range in the depth direction in the OCT data becomes wider as the sweep frequency becomes smaller.

In the wavelength sweep light source, a tilt of a phase slope may change according to the sweep frequency. That is, the correspondence relationship between the sampling timing and the wavelength of the light emitted from the light source may change non-linearly between the first frequency and the second frequency. Therefore, in order to appropriately obtain the OCT data at each of the first frequency and the second frequency, it is necessary for the conditions for mapping the sampled spectral interference signal into a wavelength space to be changed for each sweep frequency.

<Correction Processing>

The arithmetic control unit according to the first embodiment executes correction processing. In the correction processing, at least one of the control of the OCT optical system and the arithmetic processing of the spectral interference signal by the image processor is corrected according to the sweep frequency such that the change according to the sweep frequency is suppressed.

<Correction Relating to Imaging Range in Depth Direction>

The arithmetic control unit may use any one of the following methods in the correction processing to maintain the imaging range in the depth direction in the OCT data before and after the change of the sweep frequency. For example, the adjustment may be performed by any one of the following methods such that the number of samplings per one A scan is to be equal between when the sweep frequency is a first period and when the sweep frequency is a second period, to maintain the imaging range.

As a first method for maintaining the imaging range in the depth direction, the arithmetic control unit may change the sampling rate in the conversion unit according to the sweep frequency. When the sweep frequency is constant, the imaging range in the depth direction becomes wider as the sampling rate is higher. The sampling rate may be increased together with the sweep frequency to maintain the imaging range before and after the sweep frequency is changed.

As a second method for maintaining the imaging range in the depth direction, the arithmetic control unit may thin out the spectral interference signal obtained by sampling according to the sweep frequency either before or after analog-to-digital conversion. For example, by thinning out the interference signal when the sweep frequency is the smaller second frequency, the imaging range in the depth direction can be made equal to that when the sweep frequency is the larger first frequency.

As a third method for maintaining the imaging range in the depth direction, the arithmetic control unit may perform interpolation on the spectral interference signal obtained by sampling either before or after the analog-to-digital conversion. For example, by interpolating a sampling result when the sweep frequency is the larger first frequency, the imaging range in the depth direction can be made equal to that when the sweep frequency is the smaller second frequency.

<Correction Relating to Mapping>

The arithmetic control unit may change mapping information for mapping the spectral interference signal obtained by each sampling into the wavelength space according to the sweep frequency. The mapping information indicates the correspondence relationship between the sampling timing and the wavelength of the light emitted from the light source (that is, mapping condition). As calibration, a temporal change in the wavelength of the emitted light may be measured for each sweep frequency, and the mapping information for each sweep frequency may be obtained based on the measurement result. The mapping information may be, for example, a look-up table. Such mapping information is changed according to the sweep frequency, and thus it is possible to acquire appropriate OCT data at each sweep frequency based on the arithmetic processing for the spectral interference signal.

<Correction of Light Amount>

When the sweep frequency is changed, the duty ratio is changed according to the sweep frequency. As a result, sensitivity of the spectral interference signal is considered to be reduced. On the contrary, the arithmetic control unit may change an amount of the light emitted from the wavelength sweep light source for each sweep frequency.

<About Selection Method of Sweep Frequency>

The sweep frequency in the wavelength sweep light source may be selected based on an operation input from the examiner. In this case, the OCT apparatus may include an input receiving unit that receives the operation input.

The operation input may be an operation input for setting any one of a measurement site, a measurement range, and a scan pattern. That is, the sweep frequency may be automatically set according to any one of the measurement site, the measurement range, and the scan pattern, which is set based on the operation input. For example, there are cases where a first scan pattern and a second scan pattern in which a narrow range is scanned with respect to the first scan pattern are prepared as scan patterns. In this case, a first value may be selected as the sweep frequency when the first scan pattern is selected, and a second value may be selected as the sweep frequency when the second scan pattern is selected. Accordingly, it is possible to suppress a measurement time in a case where a wider range is scanned, and it is possible to obtain high-quality OCT data in a case where a narrower range is scanned.

In a case where the OCT data of the fundus is acquired, the sweep frequency in the wavelength sweep light source may be changed according to a degree of opacity of the translucent body in the eye to be examined. In this case, the OCT apparatus may have a detection unit that detects the opacity of the translucent body in the eye to be examined. The arithmetic control unit may change the sweep frequency in the light source according to the degree of opacity to be detected.

Various methods are considered as a method of detecting the opacity of the translucent body in the eye to be examined. For example, the translucent body may be imaged using the OCT optical system or a separate optical system, and the opacity may be detected from the captured image. A fundus image may be acquired, and presence or absence of significant opacity may be determined based on the fundus image (that is, opacity detection may be performed). Of course, there may be another factor other than the opacity in a case where the image quality of the fundus image is low. However, improvement can be expected even in a case where there is another factor other than the opacity.

Second Embodiment

Next, a second embodiment will be described.

With an OCT apparatus and the like according to the second embodiment, a burden on a subject due to the adjustment of an optical path length difference is reduced.

The OCT apparatus according to the second embodiment includes at least the OCT optical system, the image processor, an optical path length difference adjusting unit, and the arithmetic control unit (control means in the embodiment). The OCT apparatus according to the second embodiment is suitable for acquiring the wide-area OCT data in the depth direction. Additionally, the OCT apparatus according to the second embodiment may have a focus adjustment unit.

The OCT optical system according to the second embodiment is an OCT optical system that detects a spectral interference signal between the measurement light guided to the tissue of the eye to be examined and the reference light. The OCT optical system according to the second embodiment can acquire the wide-area OCT data in the depth direction. Such an OCT optical system may be the SS-OCT optical system. However, the present disclosure is not limited thereto and may be the SD-OCT optical system. However, in the case of the SD-OCT optical system, it is desirable to have a sufficient imaging range in the depth direction to the extent that the present invention can be implemented. In this case, full-range processing may be used.

In the second embodiment, the wide-area OCT data is acquired by the image processor based on the spectral interference signal output from the OCT optical system.

<Optical Path Length Difference Adjusting Unit>

The optical path length difference adjusting unit changes the optical path length difference between the measurement light and the reference light. Accordingly, a depth position where the OCT data is acquired is adjusted. For example, the optical path length of at least one of a measurement optical path and a reference optical path may be changed, and as a result, the optical path length difference may be changed. The optical path length difference adjusting unit may move an optical member disposed in at least one of the measurement optical path and the reference optical path by a drive unit to change the optical path length difference. The optical path length difference adjusting unit may adjust an operation distance between the eye to be examined and the apparatus to change the optical path length difference.

<Arithmetic Control Unit>

In the second embodiment, the arithmetic control unit executes adjustment processing and capture processing (capture of OCT data).

<Adjustment Processing (Adjustment Step)>

The adjustment processing will be described in detail. In the first embodiment, at least the depth position where the OCT data is acquired is adjusted in the adjustment processing. The depth position is adjusted by adjusting the optical path length difference. In the second embodiment, the depth position (and the optical path length difference) is adjusted by the adjustment processing such that a fundus image (signal corresponding to the fundus image) is included in a predetermined section (details will be described below) in the OCT data.

Figure 4:
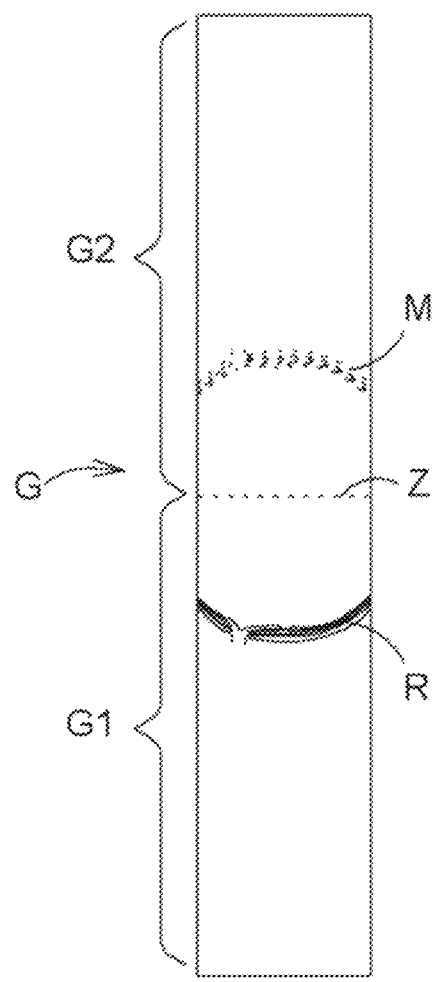
FIG. 4 is a diagram for describing OCT data.

Unless otherwise specified, the predetermined section indicates data on an one-direction side set in advance with respect to a zero delay position in the OCT data (one of first image data G1 and second image data G2 which is set in advance in FIG. 4). However, in a case where the full-range processing is performed, the present disclosure is not limited thereto. The entire OCT data (both the first image data G1 and the second image data G2 in FIG. 4) may be the predetermined section.

In the adjustment processing, other conditions such as focus and polarization may be adjusted. The adjustment of each condition may be performed in order (that is, sequentially) or in parallel.

As an initial position of the depth position, a position is set such that a first fundus position to a second fundus position are included in the predetermined section in the OCT data. The first fundus position is a fundus position assumed in an eye with short eye axial length or an eye with long eye axial length. The second fundus position is a fundus position assumed in an eye with average eye axial length. The fundus position assumed in the eye with short eye axial length may be a fundus position assumed in a child (for example, less than 22 mm from cornea). The fundus position assumed in the eye with long eye axial length may be, for example, a fundus position assumed in an intense myopic eye (for example, 26 mm or more from cornea).

In the present embodiment, the predetermined section in the OCT data is required to be sufficiently longer than a distance from the first fundus position to the second fundus position.

Although there is a variation in a value of the average eye axial length for each statistic, a value of around 24 mm is often used. There is a report of a value of about 16 mm as a case where the eye axial length is extremely short. A difference between the two values is about 8 mm. In a case where the fundus position assumed in the eye with short eye axial length is employed as the first fundus position, the distance from the first fundus position to the second fundus position may be 8 mm or more as an example. As described above, in a case where the first fundus position and the second fundus position are assumed, the predetermined section in the OCT data is required to be 8 mm or more.

In the adjustment processing, the OCT data is acquired when the depth position is the initial position. The OCT data acquired at this time may be subjected to detection processing of the fundus image (and signal corresponding to the fundus image). As a result of the detection processing, in a case where the fundus image is included in the predetermined section of the OCT data, the capture processing may be executed.

The predetermined section is a section that is an output target such as an image output, and may be a partial section of the OCT data or the entire section. In a case where the fundus image is located within the predetermined section, the capture processing may be executed regardless of the position of the fundus image. At this time, the capture processing may be executed without changing the depth position of the imaging range from the initial position.

On the other hand, in a case where the fundus image is not included in the predetermined section when the depth position is the initial position, the depth position is changed from the initial position.

<First Method>

For example, in a case where the center of the predetermined section is offset with respect to the second fundus position when the depth position is the initial position, the depth position may be changed by the following first method.

That is, in the first method, the depth position is changed from the initial position to a back side in a case where the first fundus position is the fundus position assumed in the eye with short eye axial length. The depth position is changed from the initial position to a front side in a case where the first fundus position is the fundus position assumed in the eye with long eye axial length.

In the first method, a position changed by one step from the initial position is referred to as a second position for convenience. The second position is a position such that a third fundus position is included in the predetermined section. The third fundus position is the other of one that is assumed to be the first fundus position among the fundus position assumed in the eye with short eye axial length and the fundus position assumed in the eye with long eye axial length.

Figure 7:
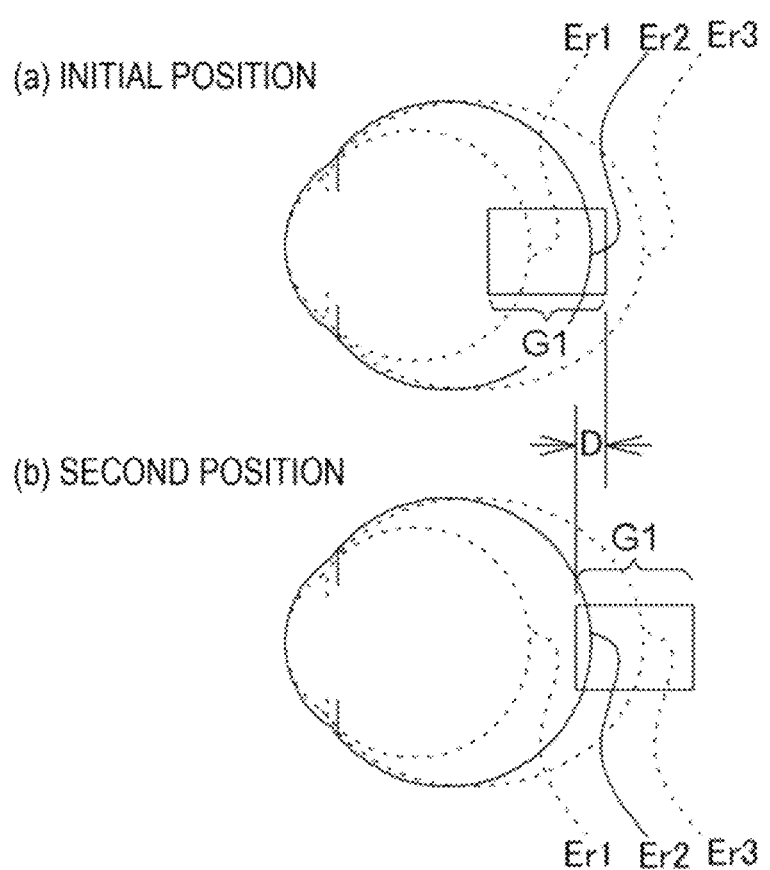
FIG. 7 is a diagram showing a first method (method in the example) of adjusting a depth position where the OCT data is acquired.

FIG. 7 shows a state where the depth position is adjusted by the first method. FIG. 7 shows the predetermined section in the OCT data as the region G1. The first fundus position, the second fundus position, and the third fundus position are respectively indicated by the reference signs Er1, Er2, and Er3. As shown in FIG. 7, in a case where the first fundus position is the fundus position assumed in the eye with short eye axial length and the third fundus position is the fundus position assumed in the eye with short eye axial length, the predetermined section is displaced in one step from the initial position as shown in (a) of FIG. 7→(b) of FIG. 7.

In a case where the fundus image is located within the predetermined section when the depth position is changed to the second position, the capture processing may be executed regardless of the position of the fundus image.

With the first method, it is possible to start capture of the OCT data with adjustment within one step (in other words, only changing from the initial value once), in most of the eyes to be examined. As a result, it is possible to quickly capture the OCT data regardless of the eye axial length of the eye to be examined.

An overlap amount of the predetermined section between the initial position and the second position (indicated by reference sign D in FIG. 7) may be half or less of the predetermined section. The imaging range of the OCT data is wide in the depth direction. Therefore, it is easy to adjust the depth position such that the fundus image is appropriately detected even though the overlap amount is half or less of the predetermined section.

<Second Method>

For example, in a case where the second fundus position is located substantially in the center of the predetermined section when the depth position is the initial position, the depth position may be changed by the following second method.

In the second method, positions changed within two steps from the initial position is respectively referred to as a third position and a fourth position for convenience.

In the second method, the depth position is sequentially changed to the third position on the front side and the fourth position on the back side with respect to the initial position. However, at a stage when the fundus image is located within the predetermined section at any one of the third position and the fourth position, the capture processing is executed regardless of the position of the fundus image.

By the way, the eye axial length of normal eyes including mild myopic eye and hyperopic eye shows a normal distribution with the second fundus position (approximately OD) as substantially the center. An eye with pathological abnormality in the eye axial length, such as intense myopic eye, does not follow the above normal distribution, but is relatively small with respect to a population parameter (normal eye) of the normal distribution. With the second method, since the second fundus position is disposed in the center of the predetermined section at the initial position, the capture is executed on a larger number of eyes to be examined without necessarily requiring the adjustment from the initial position. As a result, it is easy to shorten a time required for adjusting the depth position.

Figure 8A:
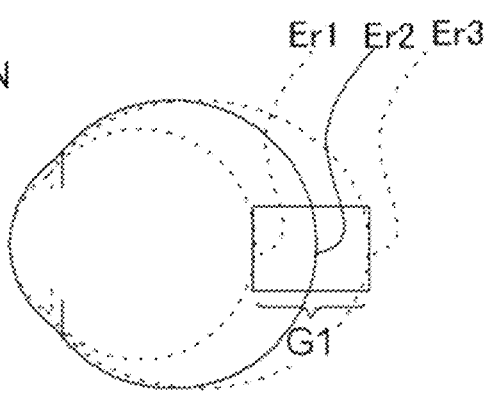
FIGS. 8A, 8B, and 8C are diagrams showing a second method (modification method of the example) of adjusting the depth position where OCT data is acquired.
Figure 8B:
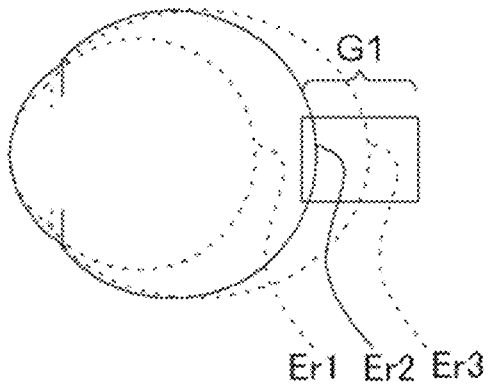
Figure 8C:
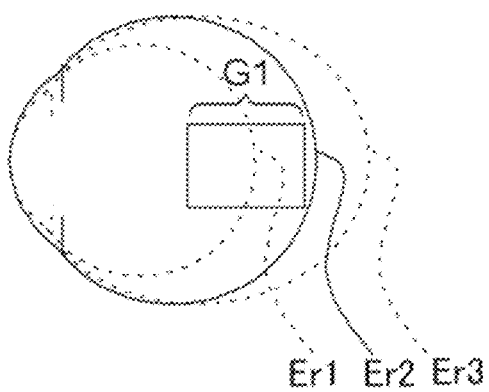

FIGS. 8A, 8B, and 8C show states where the depth position is adjusted by the second method. FIGS. 8A, 8B, and 8C show predetermined sections by the reference sign G1 as in FIG. 7. The first fundus position, the second fundus position, and the third fundus position are respectively indicated by the reference signs Er1, Er2, and Er3. In the second method, the displacement of the predetermined section is performed within two steps from the initial position as shown in FIG. 8A→FIG. 8B→FIG. 8C or FIG. 8A→FIG. 8C→FIG. 8B.

It is considered that a range of 16 mm to 32 mm from the cornea can be imaged with one shot, by using the OCT light source with high depth of penetration (for example, by using a VCSEL wavelength sweep light source) or by using the OCT light source with high depth of penetration and the full-range processing together. In this case, it is possible to start the capture without necessarily changing the depth position from the initial position in most of the eyes to be examined.

<Capture Processing (Capture Step)>

The OCT data is captured by the capture processing. For example, the measurement light is scanned along the scanning line set in advance on the tissue of the eye to be examined, and the OCT data of each of the plurality of scanning lines is acquired as imaging data. The imaging data is stored in a memory.

<Display of Imaging Result>

In the captured OCT data, the fundus image is drawn in a narrow range of the entire imaging range. Therefore, in a case where the entire imaging range is displayed on the screen as it is, the tissue of the fundus is considered to be difficult to observe. On the contrary, in the present embodiment, the following <Setting step> and <Display Control Step> may be executed when the OCT data is displayed.

<Setting Step>

In the setting step, an extraction region is set for a partial depth region in the OCT data.

The extraction region in the present embodiment will be described with reference to FIG. 4. FIG. 4 shows image data G of a tomographic image, which is an example of visualized OCT data. The image data G includes the first image data G1 corresponding to a back side of a zero delay position Z and the second image data G2 corresponding to a front side of the zero delay position Z, and the first image data G1 and the second image data G2 are symmetrical with respect to the zero delay position Z. Specifically, the real image and the virtual image of the fundus image are formed symmetrically with respect to the zero delay position Z.

In the setting step, the extraction region is set for the data in the one-direction side from the zero delay position Z (any one of the first image data G1 and the second image data G2 in FIG. 4). At this time, the depth region including an image position of the tissue is set as the extraction region. In other words, a distance between one or both of an upper end and a lower end of the extraction region and the zero delay position is adjusted such that the image position of the tissue is included between the upper end and the lower end of the extraction region.

In the setting step, the image position of the tissue in the OCT data may be detected. In this case, the distance between one or both of the upper end and the lower end of the extraction region and the zero delay position may be adjusted based on the detected image position. In this case, for example, a relationship between a reference position in the extraction region and the image position of the tissue in the OCT data is adjusted. As a result, the distance between one or both of the upper end and the lower end of the extraction region and the zero delay position may be adjusted.

In observing from a retina surface of a center portion of the fundus (between macula and papilla) to a choroid, the imaging range in the depth direction of about a few millimeters (for example, 2 mm to 3 mm) is sufficient, whereas a imaging range twice that or more (imaging range on the one-direction side from the zero delay position) may be realized in the wavelength sweep OCT. In this case, in a case where the center portion of the fundus is displayed in the extracted OCT data, it is preferable that a length of the extraction region in the depth direction is half or less than the imaging range of the OCT data which is an extraction source.

The full-ranging technique may also be applied to the OCT data according to the second embodiment. That is, the OCT data with a wider range in which the virtual image is selectively removed may be acquired. In this case, it is possible to set the extraction region at any depth position from a region where the first image data G1 and the second image data G2 are combined.

<Display Control Step>

In the display control step, the extracted OCT data corresponding to the extraction region is extracted from the OCT data and displayed on a monitor in a display region set in advance. In the present embodiment, the depth region including the image position of the tissue is extracted from the OCT data and displayed instead of the entire OCT data even in a case where the OCT data with high depth of penetration is acquired. Therefore, the image of the tissue of the eye to be examined is displayed in a more enlarged manner in the display region set in advance. As a result, it is easy to grasp well a state of the tissue of the eye to be examined through the extracted OCT data.

<Display of Information Indicating Position of Extraction Region>

In the display control step, information indicating a position relationship of the extraction region for the OCT data which is the extraction source may be displayed on the monitor together with the extracted OCT data. With the displaying of such information, for example, it is easy to grasp the position of the tissue of the eye to be examined included in the extracted OCT data.

The information indicating the position relationship of the extraction region for the OCT data which is the extraction source may be displayed as, for example, a graphic, a text, or a combination of both. The graphic may be a thumbnail image of the OCT data which is the extraction source or may be another image. In a case where the thumbnail image of the OCT data is displayed, the extraction region may be displayed in a highlighted manner on the thumbnail image. The graphic may show a position relationship between the tissue included in the OCT data which is the extraction source and the extraction region (for example, refer to FIG. 10). Further, the graphic may be, for example, the following indicator. The indicator is a bar or a number line indicating the imaging range of the OCT data, and the range corresponding to the extraction region is emphasized in a form distinguishable from another range. The graphic may be an indicator that indicates the position relationship between the tissue included in the OCT data which is the extraction source and the extraction region by color. For example, the color of the indicator may be changed to green in a case where the extraction region includes the tissue and red in a case where the extraction region does not include the tissue.

<Changing Step>

In a changing step, an operation input for changing at least one of a depth position and a range of the extraction region for the OCT data is received. The at least one of the depth position and the range of the extraction region is changed based on the operation input.

The operation input may be input through various input interfaces.

The graphic indicating the position of the extraction region may be used as a widget for receiving an operation input in the changing step. In this case, the operation input for changing the extraction region may be input through the above graphic. As one specific example, an operation of moving a highlighted portion on the thumbnail image or the indicator may be input as the operation input for changing the extraction region. The widget here is a generic term for interface parts (UI parts) of a GUI and is also referred to as a control. Various ones such as a button, a slider, a check box, and a text box are known as specific examples of widgets.

In a case where at least one of the depth position and the range of the extraction region is changed by the changing step, the extracted OCT data displayed in a predetermined display region is switched to one corresponding to the changed extraction region in the subsequent display control step.

Accordingly, it is possible to observe, on the monitor, the tissue included in the OCT data and located at a desired depth position.

In the case where at least one of the depth position and the range of the extraction region is changed by the changing step, a display form of the extracted OCT data on the monitor may be changed according to the changed extraction region in the subsequent display control step.

In the present embodiment, the changing of the display form may be realized, for example, by changing a layout of the extracted OCT data on the monitor. In this case, any one of a position, a size, and a shape of the display region in which the extracted OCT data is displayed may be changed to change the layout. At least any one of a scale and an aspect ratio of the extracted OCT data in the display region according to the extraction region may be changed to change the display form. A coordinate system in the display region according to the extraction region may be changed to change the display form. In this case, the extracted OCT data is converted (transformed) according to the coordinate system. Further, some of the above examples may be combined.

In the present embodiment, OCT data including images of the plurality of tissues at different depth positions in the eye to be examined may be acquired, in an acquisition step. In this case, the display form of the extracted OCT data may be changed according to a type of tissue included in the extraction region, in the display control step. For example, the display form may be changed at least between a case where the extraction region includes only a fundus tissue and a case where the extraction region includes the translucent body. The display form may be changed according to the number of types of tissues included in the extraction region.

<Sequential Display by OCT Data of Plurality of Scanning Lines>

In the acquisition step, the plurality of OCT data for each of the plurality of scanning lines set in advance may be acquired. The plurality of scanning lines may be continuously scanned by the OCT optical system to capture the plurality of OCT data. The plurality of scanning lines may be set at positions close to each other (for example, positions separated by substantially one pixel) by a raster scan.

In this case, in the setting step, the setting processing of the extraction region with respect to each piece of OCT data may be performed such that the position of the extraction region with respect to the image position of the subject is matched between the plurality of OCT data. In the display control step, the extracted OCT extracted from each of the plurality of OCT data may be sequentially displayed in the display region. At this time, the plurality of extracted OCT data may be switched and displayed such that the position on the tissue displayed by the extracted OCT data shifts in one-direction. Accordingly, the position of the tissue image is maintained with respect to the display region in the sequential display of the plurality of extracted OCT data in the display region.

However, the present disclosure is not necessarily limited thereto. In the setting step, the setting processing of the extraction region with respect to each piece of OCT data may be performed such that the depth position of the extraction region is matched between the plurality of OCT data. In a case where the plurality of extracted OCT data are switched and displayed such that the position on the tissue displayed by the extracted OCT data shifts in one-direction, the image position of the tissue is displaced in the display region. As a result, it is easy to grasp a three-dimensional shape of the tissue in the sequential display.

<Real Time Display>

Each time new OCT data is captured through the OCT optical system, sequentially, real-time extracted OCT data may be displayed by the above sequential display. In this case, for example, in the acquisition step, each time each scanning line is scanned by the OCT optical system to generate the OCT data by the image processor, the OCT data is acquired as new OCT data at any time. The extraction region is set in the new OCT data, and the extracted OCT data corresponding to the extraction region is displayed in real time in the display region.

<Follow-Up Display>

The following processing may be performed for follow-up observation using the plurality of OCT data in which positions of the scanning lines match each other and imaging dates are different from each other.

For example, the plurality of OCT data in which the positions of the scanning lines match each other and the imaging dates are different from each other may be acquired, in the acquisition step.

In the setting step, the setting processing of the extraction region with respect to each piece of OCT data may be performed such that the position of the extraction region with respect to the image position of the subject is matched between the plurality of OCT data. In the display control step, the extracted OCT extracted from each of the plurality of OCT data may be sequentially displayed (switched and displayed) in the display region. In the display region, the extracted OCT data whose imaging dates are different from each other are switched and displayed with the positions of the images of the tissues being substantially matched. Therefore, it is easy to observe the temporal change in the tissues in which the examiner is interested.

<Display of Combined OCT Data>

The OCT data in which the extraction region is set may be combined OCT data. The combined OCT data is generated by combining the plurality of OCT data having different depth positions (for example, refer to Japanese Unexamined Patent Application Publication No. 2012-75640 by the present applicant). The combined OCT data may include at least OCT data of an anterior segment and the fundus. Further, the OCT data of the equator may be included. Even in the combined OCT data, it becomes difficult to observe individual tissues. Therefore, the extraction region may be set in a desired region and the region may be enlarged and displayed in a display region set in advance.

<Reduction of Data Other than Extraction Region>

In the OCT data with high depth of penetration, a data capacity of the OCT data may be enlarged. On the other hand, in the OCT data with high depth of penetration, it may be conceivable that the depth region occupied by the tissue of the eye to be examined is the same as before. In the present embodiment, the extraction region may be set to reduce (delete or compress) the data of the region other than the extraction region from the OCT. As a result, the data of the extraction region (that is, the extracted OCT data) may be saved in the memory instead of the original OCT data.

Third Embodiment

Next, a third embodiment will be described.

An OCT apparatus according to the third embodiment has at least the OCT optical system and the image processor. Additionally, the OCT apparatus according to the third embodiment may have the arithmetic control unit. The OCT apparatus according to the third embodiment is preferably the OCT with high depth of penetration. For this purpose, the OCT apparatus according to the third embodiment is preferably the SS-OCT, but is not necessarily limited thereto, and may be the SD-OCT.

In the OCT apparatus according to the third embodiment, preprocessing of increasing a data density as preprocessing for the arithmetic processing including a Fourier analysis is executed by the image processor. The data density here is a density of data points corresponding to the wavelength (wave number). An increase amount of the data density in the preprocessing can be changed.

The preprocessing of increasing the data density is preferably processing of lowering an apparent signal frequency of the spectral interference signal (spectral data). The preprocessing may be, for example, interpolation. A ZERO PADDING method and the like are known as specific examples of the interpolation. As a result of the preprocessing, an artifact due to analysis failure is suppressed in the OCT data based on the spectral interference signal. At this time, an effect of reducing the artifact is enhanced as the data density of the spectral interference signal is increased. However, there is a trade-off that a processing time of the arithmetic processing is increased. On the contrary, in the present disclosure, the increase amount of the data density in the preprocessing can be changed. Therefore, for example, a balance between the effect of reducing the artifact and the processing time of the arithmetic processing can be changed to a suitable balance for each situation.

In the OCT apparatus according to the third embodiment, the arithmetic control unit may set the increase amount of the data density in the preprocessing according to the depth position of a specific region in the OCT data. The specific region may be set automatically based on the OCT data obtained in advance or may be set manually.

For example, the specific region may be a region to be displayed in the OCT data. The specific region may be a region in which the image of the tissue is drawn in the OCT data.

At this time, a larger increase amount may be set as the depth position of the specific region is farther from the zero delay position in the OCT data.

In the OCT data with high depth of penetration, it may be preferable to extract and display a partial region of the OCT data, as mentioned in the first or second embodiment. The tissue may be drawn limitedly in a partial depth region of the OCT data even when the entire OCT data is displayed.

At this time, when the displayed region or the increase amount of the data density in the preprocessing for each piece of OCT data are constant, the influence of the artifact due to the analysis failure varies depending on the depth position of the displayed region. Therefore, when the image quality is optimized for each display, it may be necessary to adjust an imaging condition such as an OPL even though the OCT data with high depth of penetration is obtained.

On the contrary, as described above, the increase amount of the data density in the preprocessing is set according to the depth position of the specific region, and thus it is possible to appropriately suppress the artifact due to the analysis failure regardless of the depth position of the specific region.

In the OCT data, in a case where the image of the tissue is drawn in a wide range in the depth direction, the increase amount of the data density may be set with reference to a position farther from the zero delay position in the image of the tissue. Accordingly, it is easy to suitably suppress the artifact due to the analysis failure over the entire range of the image of the tissue.

In the third embodiment, real-time display may be executed in which the plurality of OCT data is sequentially acquired and displayed each time. While the real-time display is being executed, the arithmetic control unit may feed back the increase amount corresponding to the specific region to the arithmetic processing based on the specific region in at least any one of the plurality of OCT data. Accordingly, the real-time display by the OCT data in which the artifact due to the analysis failure is reduced well is realized.

The data density increases as the specific region is set to the position farther from the zero delay position. Therefore, the influence, such as increase in the processing time of the arithmetic processing, increase in time lag of the display in the real-time display, or decrease in an effective frame rate, along with the increase in the data density may occur. However, in a case where an imaging scale is large, for example, the OCT data in which the image of the tissue is drawn in a wide range in the depth direction is displayed in real time, the range in which the examiner is interested also becomes wide. Therefore, the above influence is considered to be less likely to stress the examiner.

In a case where the specific region is manually set, the operation input for designating the specific region on the OCT data of the entire range together with the OCT data of the entire range (however, it may be only one side from the zero delay position) may be received. At this time, for example, various UI parts described as being used for designating the extraction region in the second embodiment can be diverted to designate the specific region.

EXAMPLE

Hereinafter, an OCT system (optical coherence tomography system) shown in FIG. 1 will be described as an example.

As shown in FIG. 1, the OCT system according to the example includes at least an optical unit 10 and a control unit 50 corresponding to a computer of the present example. In the present example, the optical unit 10 and the control unit 50 are integrated as the OCT apparatus. The OCT system (OCT apparatus) according to the present example has the wavelength sweep OCT (SS-OCT) as a basic configuration.

Figure 2:
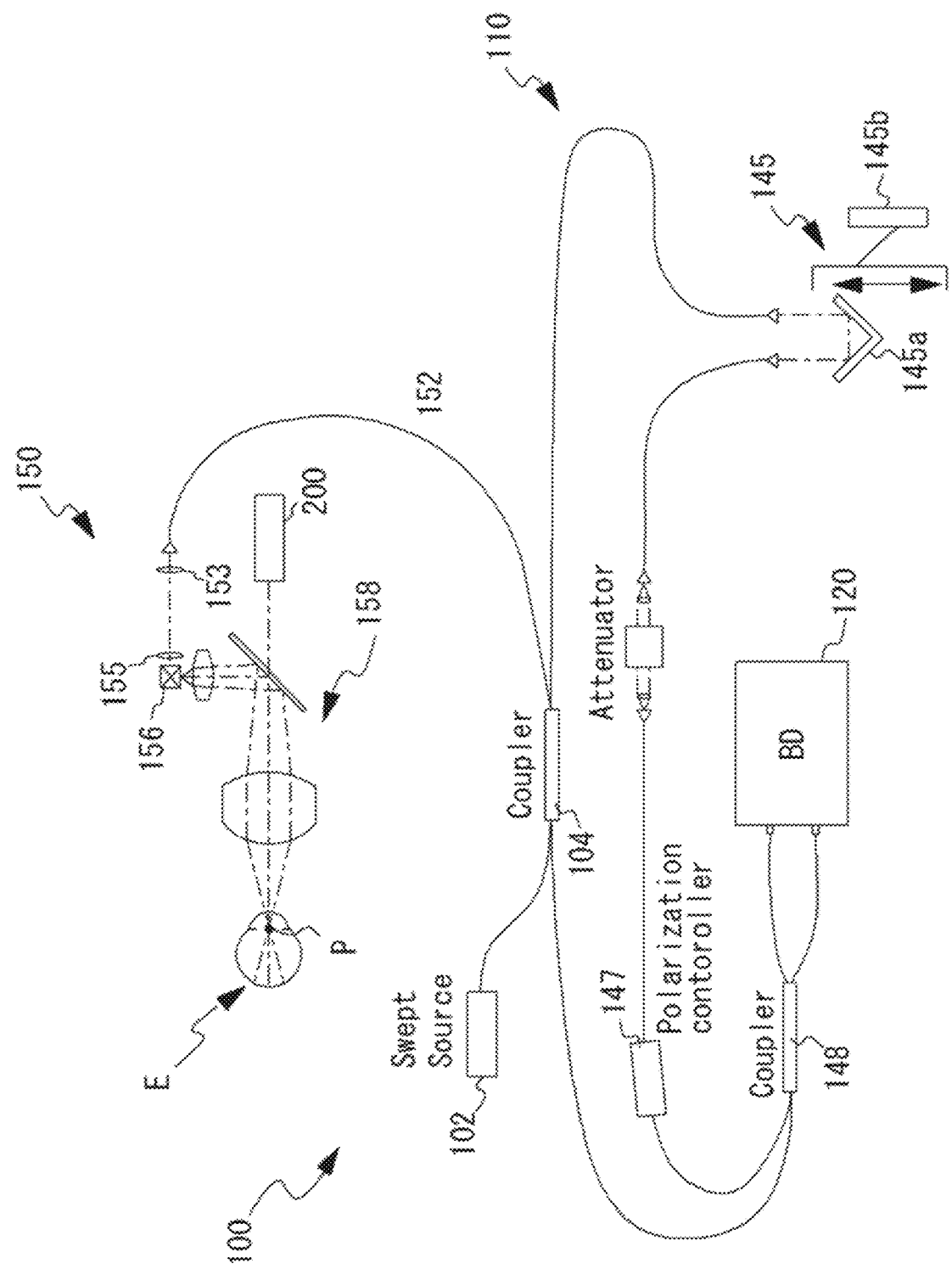
FIG. 2 is a diagram showing an OCT optical system according to the example.

The optical unit 10 includes an OCT optical system 100 (refer to FIG. 2). Further, the optical unit 10 according to the present example includes an observation optical system 200. The control unit 50 is the computer according to the present example and includes at least an arithmetic control unit (processor) 70 that controls the entire OCT system. The arithmetic control unit (hereinafter simply referred to as a control unit) 70 is configured of, for example, a CPU and a memory. As an example, in the present example, the control unit 70 also serves as the image processor in the OCT system.

In addition, the OCT system may be provided with a storage unit (memory) 72, an input interface (operation unit) 75, a monitor 80, and the like. Each unit is connected to the control unit 70.

Various programs for controlling an operation of the OCT apparatus, an initial value, and the like may be stored in the memory 72. For example, a hard disk drive, a flash ROM, and a USB memory that is detachably attached to the OCT apparatus can be used as the memory 72. The memory 72 may store various types of information on the imaging in addition to an OCT image generated from the OCT data. The monitor 80 may display the OCT data (OCT image).

<OCT Optical System>

The OCT optical system 100 in the present example will be described with reference to FIG. 2. The OCT optical system 100 guides the measurement light to an eye E to be examined by a light guiding optical system 150. The OCT optical system 100 guides the reference light to a reference optical system 110. The OCT optical system 100 causes a detector (light receiving element) 120 to receive interference signal light acquired by interference between the measurement light reflected by the eye E to be examined and the reference light. The OCT optical system 100 may be mourned in a housing (apparatus body) (not shown) and may move the housing three-dimensionally with respect to the eye E by a well-known alignment moving mechanism through an operation member such as a joystick to perform alignment with respect to the eye to be examined.

In the present example, the OCT optical system 100 uses an SS-OCT method. In this case, the OCT optical system 100 has the wavelength sweep light source as an OCT light source 102. The OCT optical system 100 has a point detector as the detector 120.

The emission wavelength of the wavelength sweep light source is swept in time. The OCT light source 102 may be the VCSEL wavelength sweep light source. The VCSEL wavelength sweep light source includes a VCSEL that performs laser oscillation and a MEMS that realizes high-speed scanning. An apparatus capable of changing the sweep frequency is used as the VCSEL wavelength sweep light source in the present example.

The detector 120 in the present example is a balanced detector that performs balanced detection using a plurality of (for example, two) detectors. The control unit 70 samples the interference signal of the reference light and return light of the measurement light according to the change of the emission wavelength by the wavelength sweep light source to obtain the OCT data of the eye to be examined based on the interference signal at each wavelength obtained by the sampling.

A coupler (splitter) 104 is used as a first light splitter and splits the light emitted from the light source 102 into the measurement optical path and the reference optical path. The coupler 104, for example, guides the light from the light source 102 to an optical fiber 152 on the measurement optical path side and also to the reference optical system 110 on the reference optical path side.

<Light Guiding Optical System>

The light guiding optical system 150 is provided to guide the measurement light to the eye E. The light guiding optical system 150 may be sequentially provided with, for example, the optical fiber 152, a collimator lens 153, a focusing lens 155, an optical scanner 156, and an objective lens system 158 (objective optical system in the present example). In this case, the measurement light is emitted from an emission end of the optical fiber 152 and becomes a parallel beam by the collimator lens 153. Thereafter, the measurement light goes toward the optical scanner 156 through the focusing lens 155. The focusing lens 155 is displaceable along the optical axis by a drive unit (not shown) and is used to adjust a light collecting state at the fundus. The light passing through the optical scanner 156 is applied to the eye E through the objective lens system 158. A first turning point PI is formed at a position conjugate with the optical scanner 156 with respect to the objective lens system 158. When the anterior segment is located at this turning point PI, the measurement light reaches the fundus without vignetting. The measurement light is scanned on the fundus according to the operation of the optical scanner 156. At this time, the measurement light is scattered and reflected by the tissue of the fundus.

The optical scanner 156 may scan the eye E with the measurement light in an XY directions (transverse direction). The optical scanner 156 is, for example, two galvanometer mirrors, and a reflection angle thereof is randomly adjusted by a drive mechanism. A reflection (traveling) direction of the light flux emitted from the light source 102 is changed, and the light flux is scanned on the fundus in any direction. As the optical scanner 156, for example, an acousto-optic modulator (AOM) that changes the traveling (deflection) direction of light may be used in addition to a reflection mirror (galvanometer mirror, polygon mirror, or resonant scanner).

The scattered light (reflected light) from the eye E due to the measurement light traces the path at the time of light projection, enters the optical fiber 152, and reaches the coupler 104. The coupler 104 guides the light from the optical fiber 152 to an optical path toward the detector 120.

<Reference Optical System>

The reference optical system 110 generates the reference light that is combined with fundus reflection light of the measurement light. The reference light that passes through the reference optical system 110 is combined with the light from the measurement optical path by a coupler 148 and interferes. The reference optical system 110 may be a Michelson type or a Mach-Zehnder type.

The reference optical system 110 shown in FIG. 2 is formed by a transmission optical system as an example. In this case, the reference optical system 110 transmits the light from the coupler 104 without returning the light to guide the light to the detector 120. Not limited thereto, the reference optical system 110 may be formed by, for example, a reflection optical system and may reflect the light from the coupler 104 by the reflective optical system to guide the light to the detector 120. In the present example, an optical path length difference adjusting unit 145 and a polarization adjusting unit 147 are disposed on the optical path from the coupler 104 to the detector 120.

The optical path length difference adjusting unit 145 is used to adjust the optical path length difference between the measurement light and the reference light. In the present example, a mirror 145a having two orthogonal surfaces is provided on the reference optical path. The optical path length of the reference optical path can be increased or decreased by moving the mirror 145a in an arrow direction by an actuator 145b. Of course, the configuration for adjusting the optical path length difference between the measurement light and the reference light is not limited thereto. For example, in the light guiding optical system 150, the collimator lens 153 and the coupler may be integrally moved to adjust the optical path length of the measurement light, and as a result, the optical path length difference between the measurement light and the reference light may be adjusted.

In the present example, the polarization adjusting unit 147 adjusts the polarization of the reference light. The polarization adjusting unit may be disposed on the measurement optical path.

<Acquisition of Depth Information>

The control unit 70 processes (Fourier analysis) the spectral interference signal detected by the detector 120 to obtain the OCT data of the eye to be examined.

The spectral interference signal (spectral data) acquired by the sampling is information indicating a relationship between wavelength and light intensity and can be represented as a function $I(\lambda)$ of wavelength $\lambda$. The function $I(k)$ may be a function that is equidistant with respect to a wave number k ($=2\pi/\lambda$), which is converted by linear regression of the function $I(\lambda)$. Alternatively, the function $I(k)$ may be acquired from the beginning as a function $I(k)$ that is equidistant with respect to the wave number k (K-CLOCK technique). As a result, the spectral interference signal in a wave number k space is obtained. An arithmetic controller may perform a Fourier analysis on the spectral interference signal in the wave number k space to obtain the OCT data in a depth (Z) region.

Further, information after the Fourier analysis may be represented as a signal including a real number component and an imaginary number component in the Z space. The control unit 70 may obtain absolute values of the real number component and the imaginary number component in the signal in the Z space to obtain the OCT data.

When the OCT data of the fundus is acquired, it is necessary to adjust the optical path length difference between the measurement light and the reference light in advance.

<Application of ZERO PADDING Method>

Figure 3:
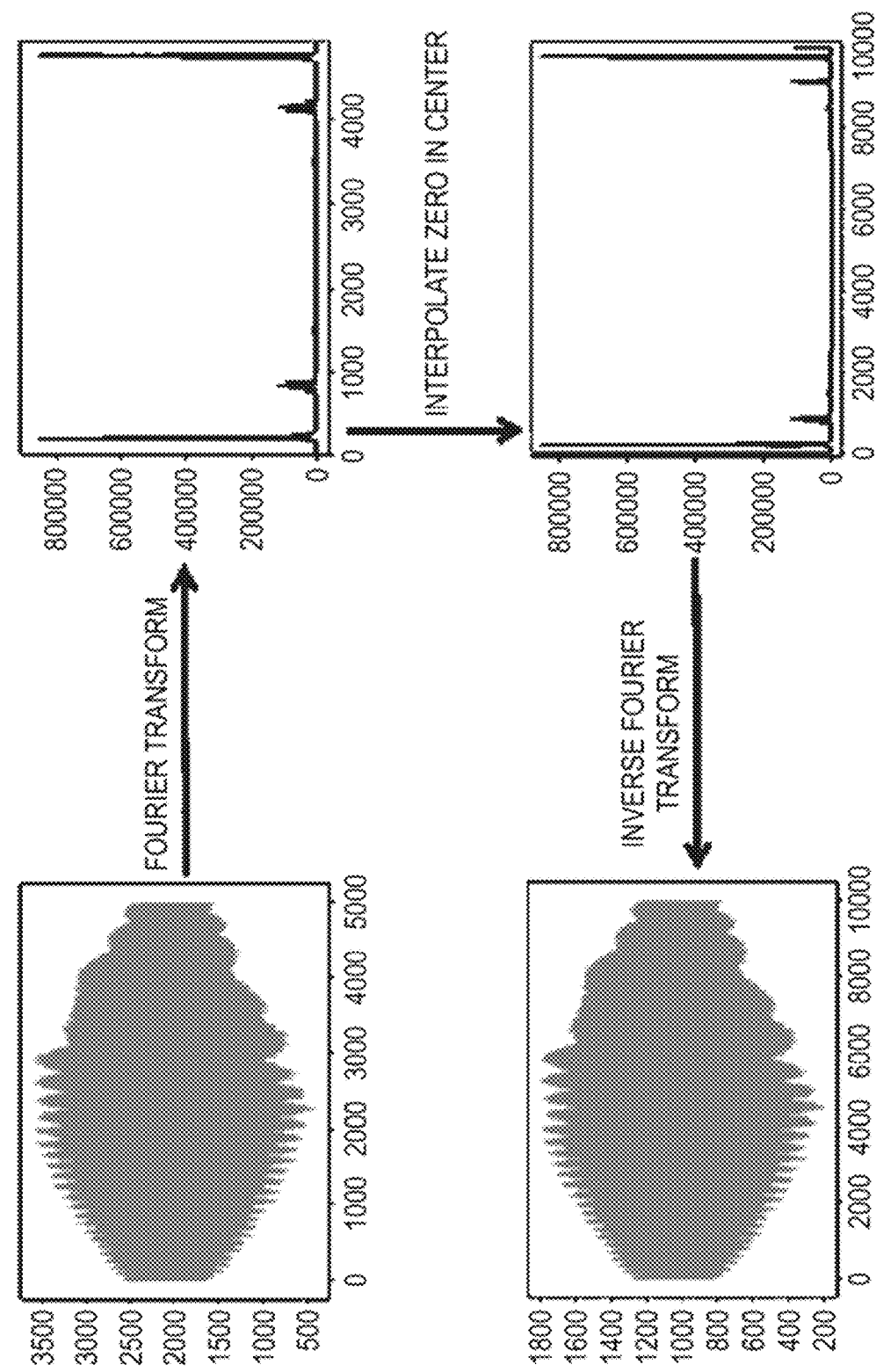
FIG. 3 is a diagram for showing an outline of a ZERO PADDING method.

In the present example, when the spectral interference signal is converted from the function $I(\lambda)$ of the wavelength $\lambda$ to the function $I(k)$ of the wave number k, data density of the spectral interference signal represented by the function $I(\lambda)$ of the wavelength $\lambda$ is increased by using the ZERO PADDING method. Specifically, as shown in FIG. 3, Fourier transform is performed on the spectral interference signal represented by the function $I(\lambda)$ of the wavelength $\lambda$ and then zero-padded (ZERO PADDING) interpolation is performed to perform inverse Fourier transform. For example, in the example of FIG. 3, the data immediately after the Fourier transform is interpolated to a center portion. In the example of FIG. 3, data having a value (coefficient of a term) of 0 is interpolated in a section of 2500 to 7500. Accordingly, data interpolated such that each Fourier expansion component of original spectral intensity has twice as many data points for each (spatial) frequency is obtained.

In the present example, the number of data to be interpolated is an amount of increase in data density. The apparent signal frequency with respect to the sampling frequency is lower as the number of data to be interpolated is larger. Therefore, when the function $I(\lambda)$ is converted into the function $I(k)$, original frequency information is guaranteed more accurately. As a result, when the Fourier analysis is performed on the spectral interference signal in the wave number k space, an artifact due to analysis failure is suppressed. An effect of suppressing the artifact by ZERO PADDING appears more clearly as non-linearity of the wavelength sweep light source (time vs. wave number) increases and depth increases.

In the present example, the number of data to be interpolated can be changed. However, unless otherwise specified, a default value is used.

<Dispersion Correction by Software>

In the present example, the control unit 70 may perform dispersion correction processing by software on the spectral data output from the detector 120. The control unit 70 obtains the OCT data based on the spectral data after the dispersion correction. Therefore, there is a difference in image quality between the real image and the virtual image (refer to FIG. 4).

That is, in the present example, a difference in a dispersion amount of the optical system between the measurement optical path and the reference optical path is corrected by signal processing. Specifically, the correction is performed by applying a correction value stored in the memory 72 in advance in the above processing of the spectral interference signal.

The control unit 70 acquires the spectral intensity of light based on a received light signal output from the detector 120 and rewrites the intensity as a function of the wavelength $\lambda$. Next, the spectral intensity $I(\lambda)$ is converted into the function $I(k)$ that is equidistant with respect to the wave number k ($=2\pi/\lambda$).

An effect of dispersion mismatch between the measurement light and the reference light shifts a phase of an interference component, lowers a peak of a combined signal of each wavelength, and makes the signal wider (lowers resolution). In the dispersion correction, the phase that is shifted for each wavelength is returned to correct the decrease in resolution due to the decrease in the interference signal. In this case, a phase shift amount $\varphi(k)$ as a function of the wave number k is obtained, and a phase shift is returned for each value of k by $I(k) \cdot \exp{-i\varphi(k)}$. A phase $\varphi(k)$ to be dispersion-corrected may be obtained in advance by calibration, or a phase $\varphi(k)$ corresponding to an acquired tomographic image may be obtained. The memory 72 stores a parameter for the dispersion correction (for example, phase $\varphi(k)$).

Thereafter, the control unit 70 performs the Fourier analysis on the spectral intensity $I(k)$ after the dispersion correction corrected by set dispersion correction data to obtain the OCT data.

For example, a first dispersion correction value (for normal image) is acquired from the memory 72 as a dispersion correction value for correcting the influence of dispersion on the real image, the spectral data output from the detector 120 is corrected by using the first dispersion correction value, and the corrected spectral intensity data is subjected to Fourier analysis to form the OCT data. A real image R is acquired as an image with high sensitivity and high resolution, and a virtual image M (mirror image) is acquired as a blurred image with low-resolution due to a difference in the dispersion correction value.

Accordingly, when a real image is acquired in a first image region G1, the real image is acquired as an image with high sensitivity and high resolution, and the virtual image (mirror image) is acquired as a blurred image with low-resolution due to a difference in the dispersion correction value in a second image region G2. On the other hand, when a real image is acquired in the second image region G2, the virtual image is acquired as a blurred image with low-resolution due to a difference in the dispersion correction value in the first image region G1.

Of course, the present disclosure is not limited thereto, and software dispersion correction may be performed on the virtual image M. In this case, the virtual image M is acquired as an image with high sensitivity and high resolution, and the real image R is acquired as a blurred image with low resolution.

For details of the method of performing the dispersion correction by software as described above, refer to U.S. Pat. No. 6,980,299, JP-T-2008-501118, and the like. Also, refer to JP-A-2010-29648.

When the OCT data at the center portion of the fundus is obtained in a case where the dispersion correction processing is performed by software, for example, the control unit 70 may extract image data having higher sensitivity and resolution from the image data of the real image and the virtual image.

<Operation Description>

The operation of the OCT apparatus according to the present example will be described based on a flowchart.

Figure 5:
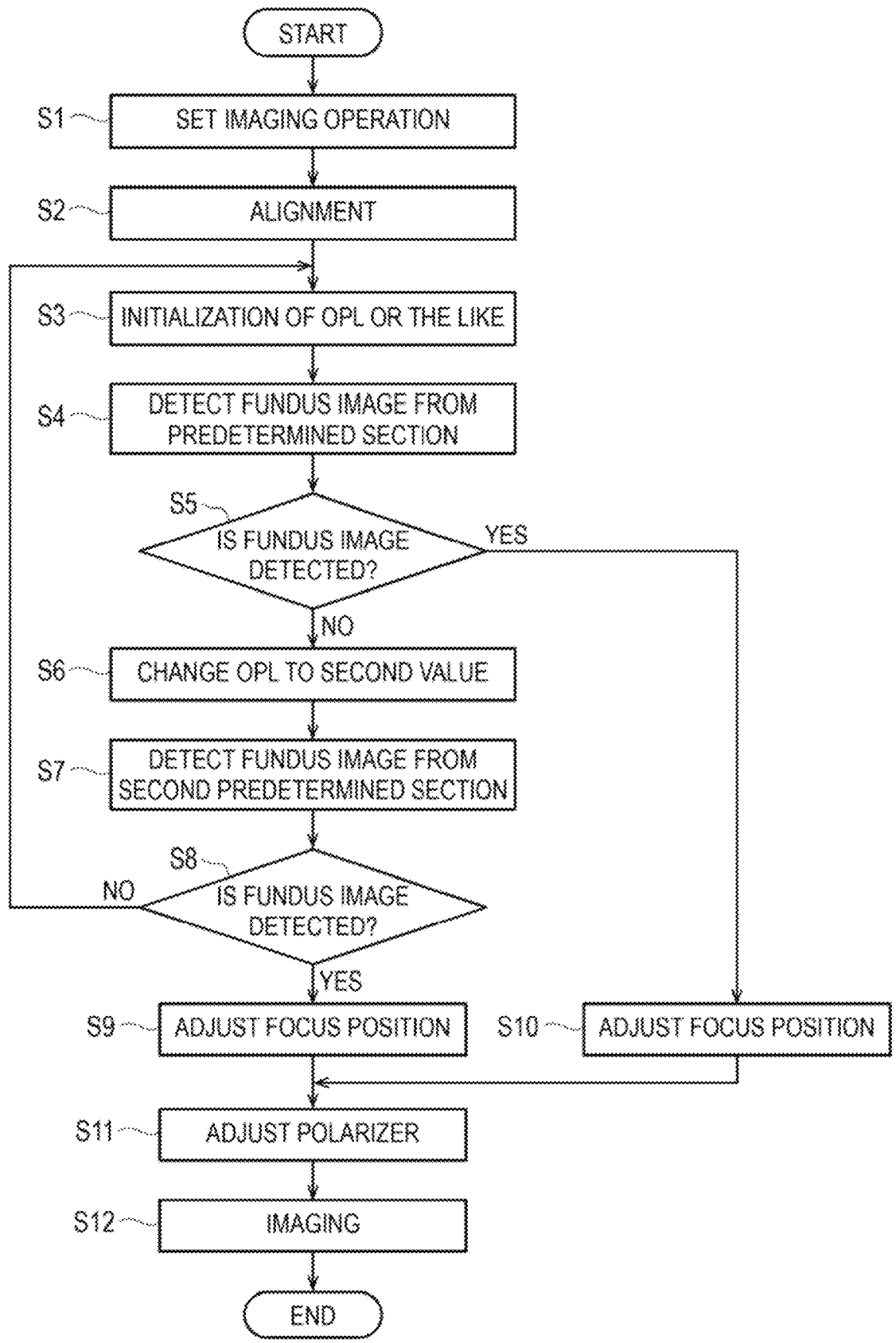
FIG. 5 is a flowchart for describing an operation up to imaging.

First, a flow until the imaging will be described with reference to a flowchart in FIG. 5.

<Setting of Imaging Operation>

First, an imaging operation is set (S1). For example, an imaging site of the eye to be examined, the scan pattern, an imaging type, and the like may be set at this time. A setting screen may be displayed to set the imaging operation.

In the present example, it is possible to set the image quality on the setting screen. For example, an image quality mode can be switched between a first mode for obtaining higher image quality OCT data and a second mode for obtaining normal image quality OCT data. The image quality is changed by changing the sweep frequency between the first mode and the second mode. In the present example, the sweep frequency in the first mode is $\Omega A$, and the sweep frequency in the second mode is $\Omega B$ (where $\Omega B > \Omega A$).

A duty ratio of the light source is the same in each mode. A state of wavelength sweep in the light source 102 is shown in FIG. 6 in a case where the wavelength space is converted into a wave number space.

Figure 6:
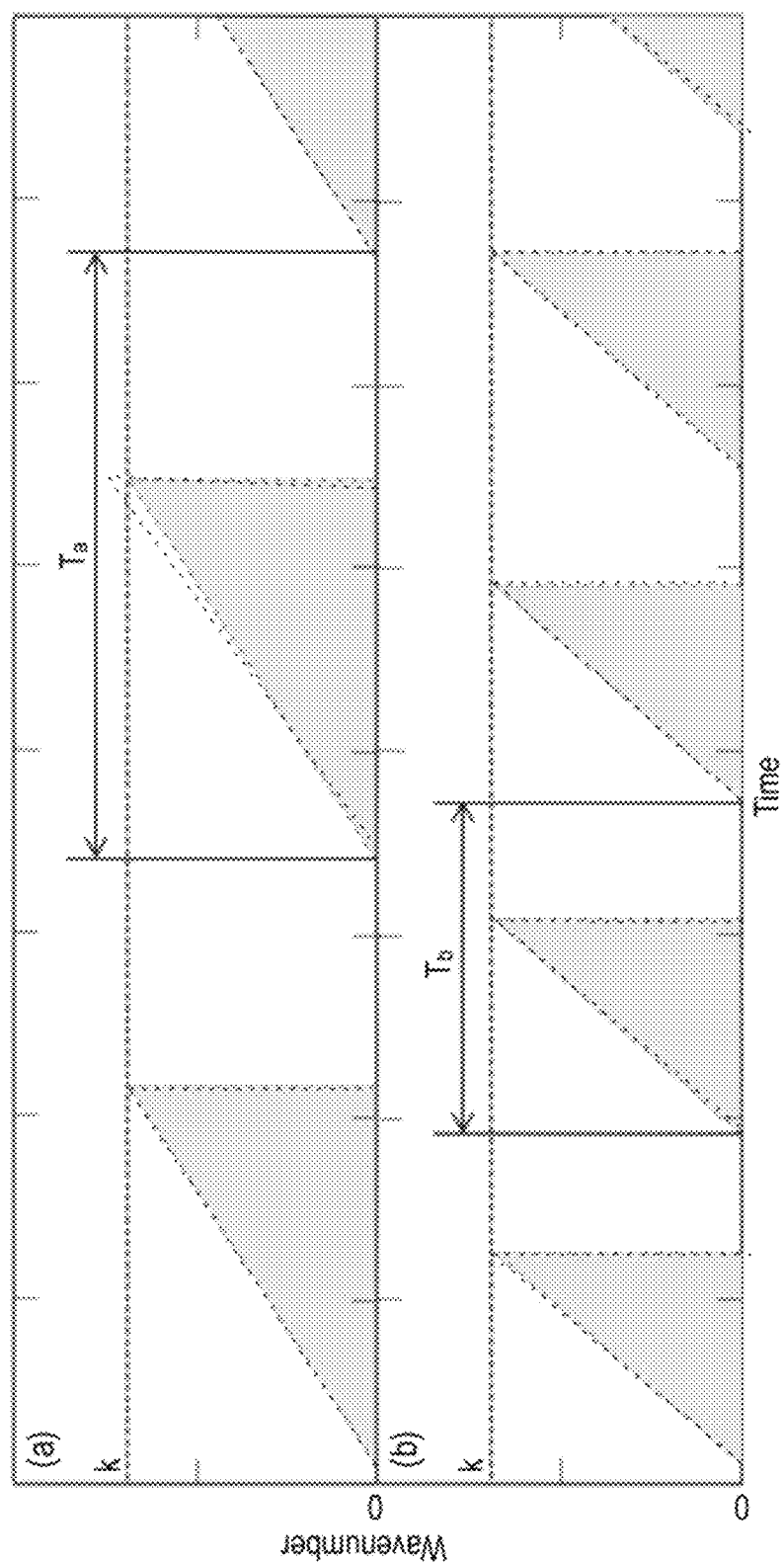
FIG. 6 is a diagram showing a state of wavelength sweep at each sweep frequency.

In FIG. 6, the sweep frequencies $\Omega A$ and $\Omega B$ are $\Omega A=1/Ta$ and $\Omega B=1/Tb$. In addition, Ta is a cycle in the first mode, and Tb is a cycle in the second mode. The wave number $k=\lambda/2\pi$ is assumed to be swept linearly with respect to time.

An SN ratio of the OCT data in each mode shown above will be reviewed.

In a case where a digitizer sampling period is the same in each mode, a relationship between the number of times of sampling Na during the sweep in the first mode and the number of times of sampling Nb during the sweep in the second mode is expressed by the following equation (1).

$$N_a = N_b \frac{T_a}{T_b} \quad (1)$$

When the coherence lengths of the measurement light and the reference light are the same between the first mode and the second mode, the quotient of the SN ratio in each mode is expressed by the following equation (2).

$$\frac{SNR_{(a)}}{SNR_{(b)}} = \frac{T_a}{T_b} \quad (2)$$

Note that SNR(a) is the SN ratio in the first mode, and SNR(b) is the SN ratio in the second mode.

Therefore, as shown in FIG. 6, in a case where Ta>Tb, improvement in the SN ratio is expected by changing the mode from the second mode to the first mode. Therefore, higher quality OCT data can be obtained in the first mode compared with the second mode.

However, although the coherence length is constant in the above description, a wavelength sweep speed and the coherence length actually have a trade-off relationship. Therefore, a larger improvement in the SN ratio is expected by changing the mode from the second mode to the first mode.

At this time, in the present example, the sampling rate in the digitizer is changed according to the sweep frequency to suppress the change in the imaging range in the depth direction between the first mode and the second mode. Specifically, the sampling rate is increased together with the sweep frequency to suppress the changes in the imaging range between the modes.

In the present example, the mapping information for mapping the spectral interference signal obtained by each sampling into the wavelength space may be changed according to the sweep frequency. The mapping information indicates the correspondence relationship between the sampling timing and the wavelength of the light emitted from the light source (that is, mapping condition). In the present example, the lookup table prepared in advance for each mode is used as the mapping information. The look-up table shows the temporal change in the wavelength of the emitted light for each sweep frequency. With the change of the mapping information according to the sweep frequency, appropriate OCT data is acquired at each sweep frequency based on the arithmetic processing for the spectral interference signal.

<Alignment>

Alignment of the apparatus is performed for the eye to be examined (S2). For example, a position relationship between the eye to be examined and a measurement light axis is adjusted based on an anterior segment observation image captured by a camera for anterior segment observation (not shown), after causing the subject to gaze at a fixation target in advance. For example, the center of the pupil of the eye to be examined and the measurement light axis are adjusted to match with each other. The alignment may be adjusted manually or automatically. At a position where the alignment adjustment is completed, an en face image of the fundus can be acquired by the observation optical system 200 as an observation image.

After the alignment is completed, the acquisition of the observation image through the observation optical system 200 and display of the observation image on the monitor 80 are started. The control unit 70 acquires the OCT image through the OCT optical system 100 at any time.

<Optimization Control>

Next, optimization control of the imaging condition is performed (S3 to S11). With the optimization control, a fundus site desired by the examiner can be observed by the OCT optical system 100 with high sensitivity and high resolution. In the present example, optical path length adjustment, focus adjustment, and adjustment of a polarization state (polarizer adjustment) are executed as an example of the optimization control in the OCT optical system 100.

For example, the optimization control is started by an operation of an optimization start button (optimize button) (not shown) as a trigger.

<Initialization of Imaging Condition>

First, the control unit 70 executes initialization processing of the imaging condition (S3). In the present example, at least the OPL and a focus position are initialized in the initialization processing. For example, each of a position of the focusing lens 155 and a position of the mirror 145a is moved to a predetermined initial position (movement start position). The mirror 145a is moved to the initial position to set a depth position where the OCT data is acquired to the initial position.

In the present example, when the mirror 145a is in the initial position (that is, when the depth position is the initial position), the first fundus position Er1 to the second fundus position Er2 is included in the predetermined section of the OCT data (image region G1 in FIG. 7), as shown in (a) of FIG. 7. The first fundus position Er1 in the present example is a fundus position assumed in the eye with short eye axial length. As one specific example, a position 16 mm from the cornea on the back side is used as the first fundus position Er1. The second fundus position Er2 in the present example is a fundus position assumed in an average eye to be examined. As one specific example, a position 24 mm from the cornea on the back side is used as the second fundus position Er2.

As an example, a position (corresponding to ±0 D) corresponding to the second fundus position Er2 is set as the initial position of the focusing lens 155. However, the initial position of the focusing lens 155 is not necessarily limited thereto and may be, for example, a movement limit position of the focusing lens 155 or another position.

<Detection Processing at Initial Position>

In the present example, the OCT data is acquired when the depth position is the initial position. The detection processing of the fundus image is performed on the acquired OCT data (S4, S5). In a case where the fundus image is detected within the predetermined section (S5: Yes), the OPL adjustment is completed without moving the OPL.

<OPL Adjustment>

On the other hand, in a case where the fundus image is not detected within the predetermined section (S5: No), the mirror 145a is moved such that the OPL is changed to the predetermined second value (S6). Accordingly, the depth position where the OCT data is acquired is shifted to the second position on the far back side. As shown in (b) of FIG. 7, in the present example, when the depth position is the second position, at least the third fundus position Er3 is included in the predetermined section of the OCT data. In the present example, as an example, a position 32 mm from the cornea on the back side is used as the third fundus position Er3.

<Detection Processing at Second Position>

The OCT data is acquired when the OPL is the second value, and the detection processing of the fundus image is performed on the acquired OCT data (S7, S8). The OPL adjustment is completed in a case where the fundus image is detected within the predetermined section. Eye axial length values of most of the eyes to be examined are included in the range of 16 mm to 32 mm from the cornea corresponding to the first fundus position Er1 to the third fundus position Er3. Therefore, the OPL adjustment is completed in most of the eyes to be examined at this stage (that is, before the OPL is changed by at most one step).

On the other hand, in a case where the OCT data is not detected when the OPL is the second value, the OPL may be readjusted such that the imaging range of the OCT data is set further on the back side. Alternatively, there may be a case where the OCT data is not properly acquired because an eyelid is closed when the OCT data is acquired, or the like. The processing after S3 may be retried. That is, the detection processing of the fundus image may be executed after the OPL is set again for at least one of the initial value and the second value.

In the present example, the optimization control of the focus position in OCT is executed after the OPL adjustment (S9, S10). Specifically, the focusing lens 155 is adjusted to a position corresponding to the fundus image detected by the detection processing.

In the OCT data acquired when the depth position is the initial position, the focusing lens 155 is moved from the position corresponding to the initial position ±0 D to a plus side when the fundus image is detected within the predetermined section (S10). That is, a condensing position of the measurement light is moved from the second fundus position to the front side. On the other hand, in the OCT data acquired when the depth position is the second position, the focusing lens 155 is moved from the position corresponding to the initial position ±0 D to a minus side when the fundus image is detected within the predetermined section (S9). That is, the condensing position of the measurement light is moved from the second fundus position to the back side. In this manner, a direction in which the focusing lens 155 is moved is appropriately set according to the position of the fundus.

In the optimization control of the focus position, focus position information of the OCT optical system 100 may be acquired based on the acquired OCT data, and the focusing lens 155 may be adjusted. At this time, a movement amount of the focusing lens with respect to the position of the fundus image in the OCT data may be set in advance experimentally or by simulation. For example, the position of the focusing lens 155 may be adjusted such that the focus position matches a predetermined layer.

The optimization control of the focus position is not necessarily limited thereto. For example, an optimum focus position may be detected using the observation image.

<Polarizer Adjustment>

In the present example, the control unit 70 drives the polarizer 147 to adjust the polarization state between the measurement light and the reference light (S11). A stronger interference signal can be obtained in a case where the polarization states of the measurement light and the reference light match. The polarizer 147 is drive-controlled based on an output signal output from a light receiving element 120 such that the polarization states between the measurement light and the reference light match.

More specifically, in the present example, the polarizer 147 is drive-controlled based on the OCT image. The control unit 70 obtains signal intensity of the OCT image acquired each time the change is made while changing a position (orientation) of the polarizer 147. For example, the signal intensity may be indicated by an evaluation value (peak value). A position of the polarizer 147 at which the evaluation value peaks is obtained, the adjustment is performed to the position, and the polarizer adjustment is completed.

With the completion of the optimization control as described above, the fundus site desired by the examiner can be observed with high sensitivity and high resolution.

<Imaging of OCT Image>

In the present example, when the examiner presses an imaging switch (not shown) after the optimization is completed, the OCT image is captured through the OCT optical system 100 (S12). The captured OCT image is stored in, for example, the memory 72. At this time, the OCT data may be captured in any one of the plurality of predetermined scan patterns.

The captured OCT data may be stored (saved) in the memory of the apparatus in association with a scan position and identification information indicating an imaging date and time. Accordingly, the captured OCT data is acquired by the control unit 70 as a captured image. When a plurality of slices are imaged at one time, each slice may be acquired.

At this time, in the present example, a predetermined one of the first image region G1 and the second image region G2 that sandwich the zero delay position Z is extracted and acquired as the captured image. At this time, one image region acquired as the captured image includes an image of the eye to be examined, which is drawn with higher sensitivity and higher resolution than the other image region, as a result of the dispersion correction described above.

<Display Control of OCT Image>

Figure 9:
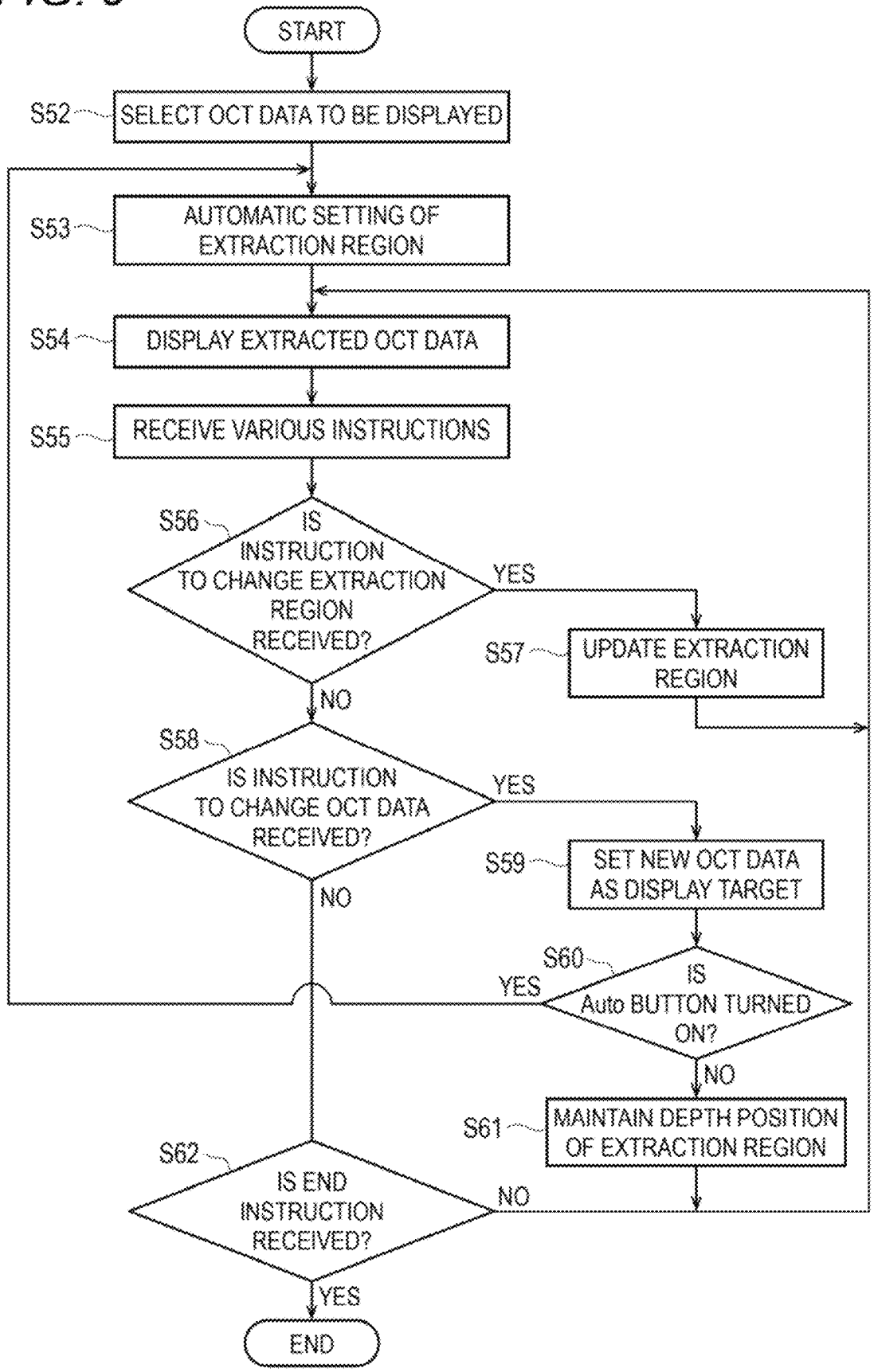
FIG. 9 is a flowchart showing a flow of processing relating to display of captured OCT data.

The ophthalmologic image processing method executed by the OCT system according to the present example will be described with reference to a flowchart shown in FIG. 9. Each piece of processing of the flowchart may be executed by the control unit 70 based on an ophthalmologic image processing program. In the present example, at least the extracted OCT data is displayed in a manner as shown in FIGS. 10 to 12 by executing each piece of processing of the flowchart.

Figure 10:
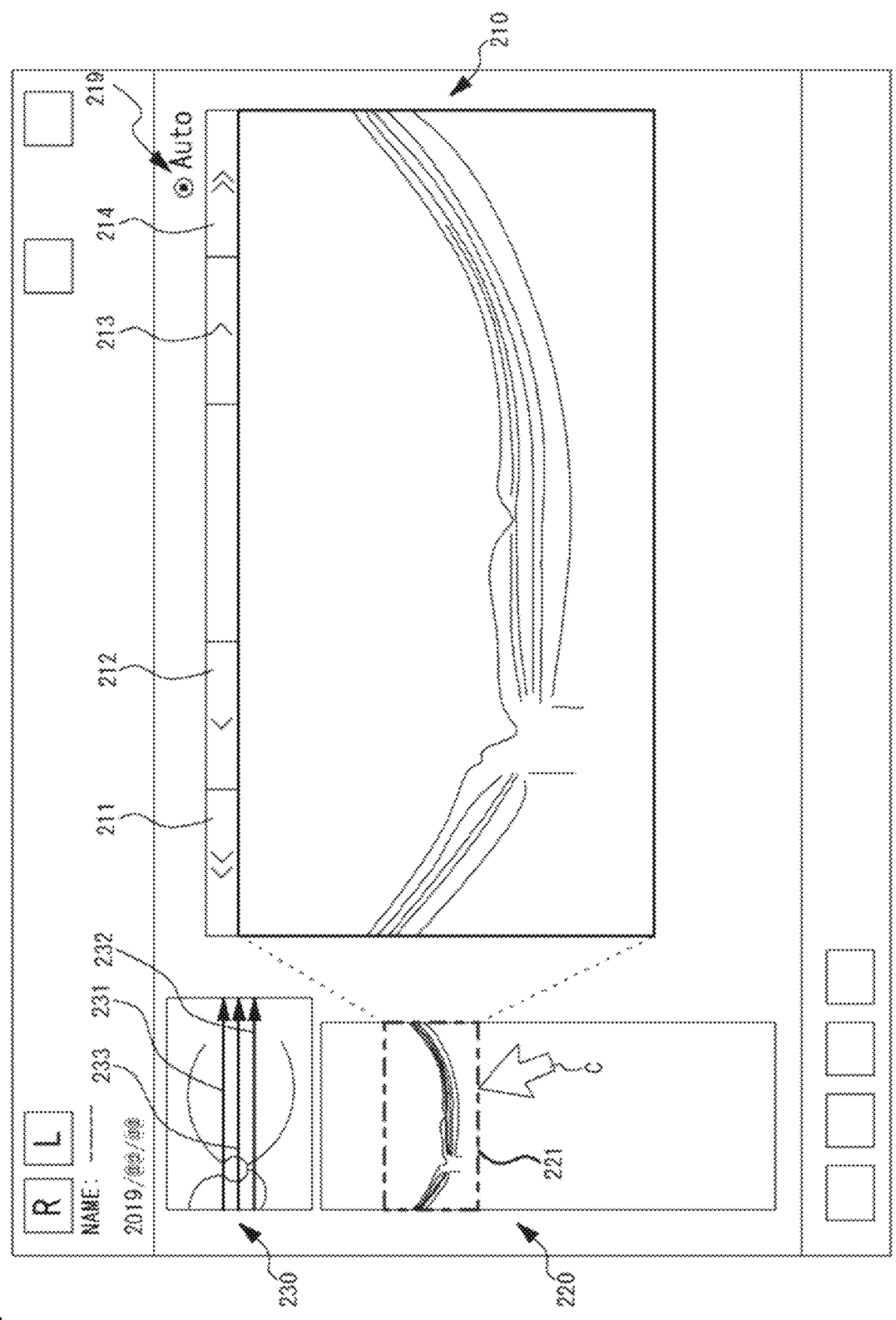
FIG. 10 is a diagram showing an example of a viewer screen.
Figure 11:
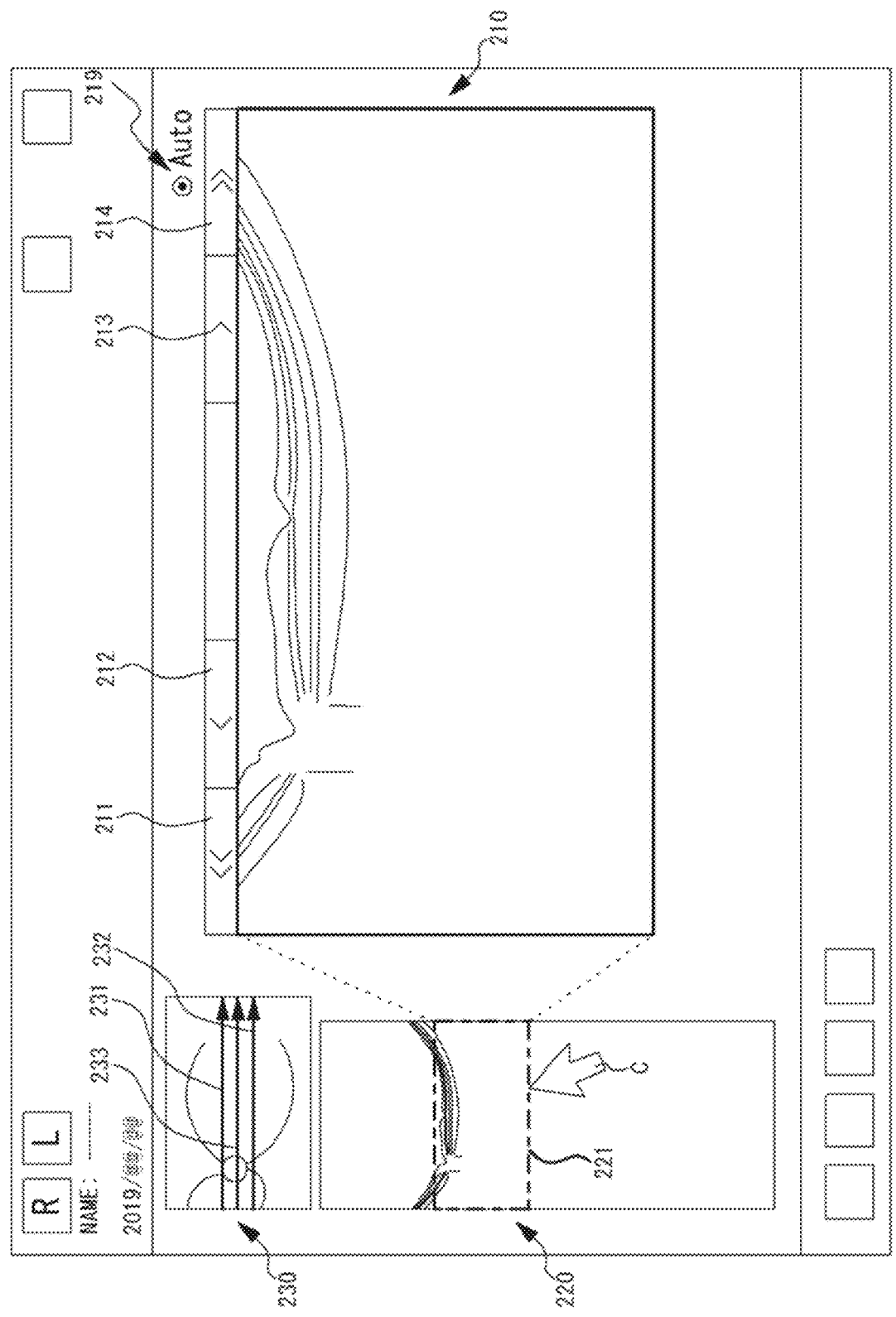
FIG. 11 is a diagram showing a viewer screen in a state where an extraction region is changed, as compared with FIG. 10.
Figure 12:
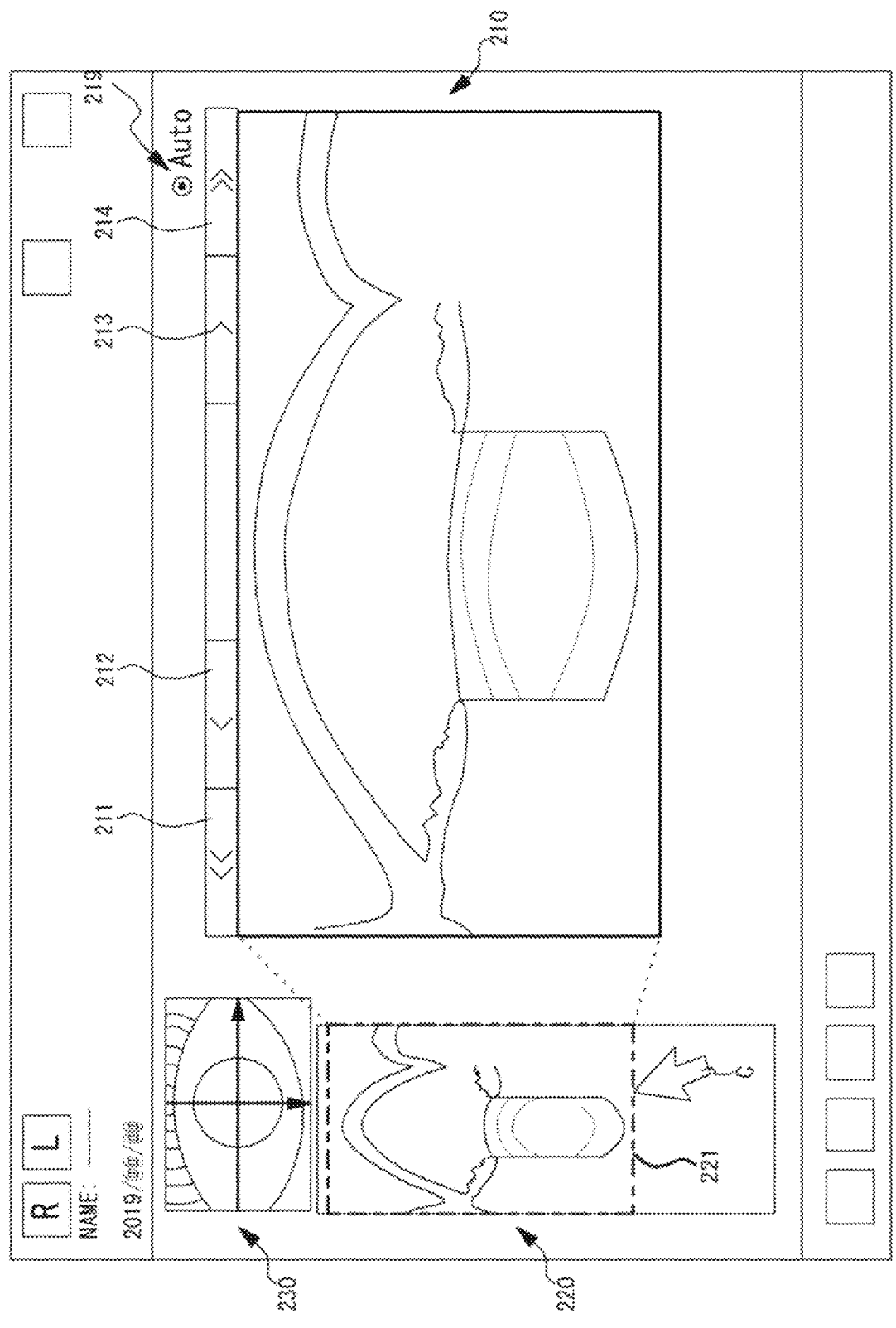
FIG. 12 is a diagram showing an example of a viewer screen when an anterior segment OCT data is displayed.

Screens shown in FIGS. 10 to 12 are referred to as viewer screens for convenience, and it is assumed that the OCT data is displayed after the imaging is completed. Further, for convenience, all OCT data in the following description is B scan data. The OCT data corresponding to the scanning line is also referred to as the slice.

<Selection of Display Target>

In the present example, the OCT data is acquired by the processing of S12 performed in advance. At this time, in a case where the plurality of slices are acquired, a slice displayed first on the screens shown in FIGS. 10 and 11 is selected (S52). The slice displayed first may be set in advance for each scan pattern.

As an example, the examples of FIGS. 10 and 11 show display examples of slices imaged by the scan pattern of "multi". In this case, each slice is acquired based on a scan in a horizontal direction. Scanning lines 231 to 233 corresponding to the respective slices are set to be different from each other in a vertical direction. In this case, as shown in FIGS. 10 and 11, a slice corresponding to the scanning line 231 passing through the fovea may be set in advance to be selected as the slice displayed first.

<Automatic Setting of Extraction Region (Setting Step of Present Example)>

The extraction region in the slice selected as a display target is set (S53). In the present example, the fundus image included in the slice may be detected by the image processing or the extraction region may be set with reference to the detection position of the fundus image.

The fundus image may be detected, for example, based on an intensity distribution of a signal in the depth direction of the OCT data, based on a characteristic amount of the image, or by another detection method.

A size of the extraction region set in step of S52 may be set in advance. In this case, a distance between the zero delay position and the extraction region is adjusted such that the detected image position is included between an upper end and a lower end of the extraction region.

<Display of Extracted OCT Data>

After the setting of the extraction region, the display of the extracted OCT data is started (S54). As an example, the display is performed in the manner as shown in FIGS. 10 and 11.

As shown in FIGS. 10 and 11, the extracted OCT data is displayed in a first display region 210 set in advance on the viewer screen.

In the viewer screens shown in FIGS. 10 and 11, a second display region 220 is provided at a position different from that of the first display region 210. The second display region 220 is also referred to as a thumbnail display region. The entire slice which is an extraction source of the extracted OCT data is displayed in the second display region 220 as a thumbnail. That is, in the present example, the extracted OCT data and the OCT data which is an extraction source of the extracted OCT data are displayed simultaneously in different display regions. At this time, the extracted OCT data is enlarged and displayed with respect to the thumbnail.

The second display region 220 displays a selection frame 221 together with the thumbnail. An extraction position of the extracted OCT data is graphically shown by the selection frame 221. In the present example, the selection frame 221 indicates a position relationship of the extraction region for the OCT data which is the extraction source.

Text information indicating the depth position of the extraction region may be displayed on the viewer screen. The text information may indicate the position of the extraction region with reference to the origin position (zero delay position), for example, a Z coordinate of the extraction region, or an optical path length from the origin position to the extraction region.

Additionally, the en face image of the fundus may be displayed in a third display region 230 on the viewer screen. The scanning line may be superimposed on the en face image. In FIGS. 10 and 11, the scanning line 231 corresponding to a currently displayed slice and the scanning lines 232 and 233 corresponding to other slices that can be displayed by switching from the currently displayed slice are displayed on the en face image.

<Reception of Various Operation Inputs>

In a state where the viewer screen is displayed, the control unit 70 can receive various instructions based on the operation input to an input interface 75 (S55). For example, a pointer C may be moved through the input interface 75 to select various widgets. Various operation inputs are input through the various widgets.

<Change of Extraction Region>

In the present example, the control unit 70 may receive a change instruction for changing the extraction region while maintaining the slice to be displayed in the state where the viewer screen is displayed. The instruction to change the extraction region may be received based on the operation input through the selection frame 221 (an example of widget) described above. In a case where the instruction to change the extraction region can be received (S56: Yes), the extraction region is updated (newly set) according to the instruction (S57).

For example, the position of the extraction region may be changeable based on the instruction. In this case, the selection frame 221 may be movable in the vertical direction on the screen based on the operation through the input interface. With the input of the operation to move the selection frame 221, the position of the extraction region in the OCT data may be changed while maintaining a size and shape of the selection frame 221.

For example, the size of the extraction region may be changeable based on the instruction. In this case, the size of the selection frame 221 may be changeable on the screen based on the operation input for each control point of the selection frame 221.

The operation input for changing the position of the extraction region and the operation input for changing the size of the extraction region may be different. At this time, the extraction region (in other words, region inside the selection frame 221) and the selection frame 221 may be set as widgets that can be individually selected (designated) as operation targets to be able to individually input the two types of operation inputs described above.

When the extraction region is updated (newly set) in response to the instruction to change the extraction region (S57), the extracted OCT data corresponding to the updated extraction region is newly displayed in the first display region 210 (S54). As a result, a part desired by the examiner can be observed in the first display region 210 in an enlarged manner even from OCT data that is long in the depth direction.

As an example, the depth position of the extraction region in the OCT data is changed to a deeper position as compared with FIG. 10, and thus the screen as shown in FIG. 11 is newly displayed.

In a case where the size of the extraction region is changed, a layout of the first display region 210 on the screen may be adjusted according to the changed size. For example, a range occupied by the first display region 210 on the screen may be adjusted. The range occupied by the first display region 210 on the screen may be constant, and vertical and horizontal scales of the extracted OCT data may be individually changed according to the shape of the first display region 210.

In a case where the position of the extraction region is changed, a displacement amount between the changed extraction region and the extraction region set in the processing of S53 may be stored in the memory 72. In a case where the size of the extraction region is changed, information specifying the changed size may be stored in the memory 72.

<Change of OCT Data to be Displayed>

In the present example, the control unit 70 may receive a change instruction for selecting a new slice as the display target in the state where the viewer screen is displayed. In the present example, the instruction to change the OCT data may be received based on an operation input for selecting a scanning line corresponding to the new slice on the en face image and an operation input for feed buttons 211 to 214.

In a case where the instruction to change the slice is received (S58: Yes), the new slice corresponding to the instruction is selected as the display target (S59).

Next, the extraction region is set for the new slice (OCT data). At this time, in the present example, a setting method of the extraction region differs depending on whether an Auto button 219 shown in FIGS. 10 and 11 is On or Off in advance as a check box.

In a case where the Auto button 219 is turned on in advance (S60: Yes), the setting processing of the extraction region for the new slice is performed such that the positions of the extraction region with respect to the image position of the fundus are matched between the slices before and after the change (S53).

Specifically, in a case where the Auto button 219 is turned on in advance (S60: Yes), the extraction region is automatically set based on the image position of the fundus image in the new OCT data.

At this time, in the present example, it may be conceivable that the extraction region in immediately preceding (displaying) OCT data is changed from the initial setting position based on the instruction to change the extraction region. In this case, the position of the extraction region with respect to the new OCT data may be set in consideration of the displacement amount of the extraction region before and after the change, which is saved in the memory in step of S57. For example, the extraction region may be set at a position offset from the image position of the fundus image in the new OCT data according to the displacement amount stored in the processing of S57.

The displacement amount may be obtained by performing matching processing between the immediately preceding OCT data and the new OCT data, and the extraction region with respect to the new OCT data may be set based on the displacement amount.

Accordingly, the site that is enlarged and observed by the extracted OCT data is maintained before and after the change of the OCT data to be displayed, and thus it is easy to intensively observe a specific site.

On the other hand, in a case where the Auto button 219 is turned off in advance (S60: No), the setting processing of the extraction region for the new slice is performed such that the depth positions of the extraction region are matched between the slices before and after the change (S61). The depth position of the extraction region in the immediately preceding (displaying) OCT data (for example, the Z coordinate of the extraction region or the optical path length from the origin position to the extraction region) is inherited as the depth position of the extraction region in the new OCT data. As a result, an appearance position of the fundus image in the extracted OCT data may change before and after the slice change according to an actual fundus shape. Accordingly, the examiner can easily grasp a three-dimensional shape of the fundus tissue from the appearance position of the fundus image in the extracted OCT data.

<Display End>

For example, in the present example, an instruction to end the display of the viewer screen may be received. In a case where the instruction is received (S62: Yes), the control unit 70 ends the display of the viewer screen.

MODIFICATION EXAMPLE

Although the present disclosure has been described based on the embodiment and the example, the present disclosure is not necessarily limited thereto and various modifications are allowed.

For example, in the above example, in the case where the OCT data is displayed after the imaging is completed, the case where the extracted OCT data is displayed has been described. However, the present disclosure is not necessarily limited thereto. For example, the display of the extracted OCT data may be executed based on the OCT data acquired in real time during the imaging of the OCT data or during the adjustment of the OCT optical system 100 during the imaging.

At this time, according to the extraction position in the OCT data of the extraction source, an amount of data interpolated in the ZERO PADDING method performed as a preprocessing for converting the spectral interference signal into the OCT data may be changed according to the extraction position of the extracted OCT data. Specifically, the amount of data to be interpolated may be increased as the extraction position is farther from the zero delay position. Accordingly, the extracted OCT data in which the artifact due to the analysis failure is suppressed can be displayed in real time, regardless of the extraction position set by the examiner. The amount of data to be interpolated and the preferable amount of data for each depth may be set as appropriate in a range in which the artifact in the extracted OCT data is visually suppressed.

The operation input for changing the extraction position may be received as appropriate while the extracted OCT data is displayed in real time. The extraction position according to the operation input is changed, thus the amount of data interpolated in the ZERO PADDING method is also changed, and the changes are applied (fed back) when subsequent OCT data is generated. Accordingly, it is possible to observe the extracted OCT data in which the artifact is suppressed while the extraction position is changed in real time.

The amount of data interpolated at each extraction position may be set in advance. For example, the amount of data to be interpolated may be determined by referring to a lookup table or function defined for each extraction position.

Not only the extraction position (depth position of the extraction region for the OCT data) but also the range of the extraction region may be changeable based on the operation input. At this time, for example, the amount of data to be interpolated in the ZERO PADDING method is determined based on a depth position of a region on a distal side from the zero delay position in the extraction region, and thus the extracted OCT data in which the artifact is suppressed as a whole can be displayed.

In the above example, the OCT data of the fundus is captured through the OCT optical system 100. However, the present disclosure is not necessarily limited thereto. In the OCT having a high depth of penetration (wide imaging range in the depth direction) shown in the example, it is conceivable that the anterior segment and the fundus are imaged by switching or simultaneously with one apparatus.

In this case, as shown in FIG. 12, the extracted OCT data relating to the anterior segment may be displayed. A depth range (width in the vertical direction) of the extraction region set for the anterior segment OCT data which is the extraction source may be different from the extraction region set for the OCT data of the fundus. The extracted OCT data relating to the anterior segment may be displayed in the first display region 210 at a scale different from that of the fundus. In this manner, the extraction region is automatically set according to the site of the eye to be examined included in the OCT data, and thus it becomes easier to observe each part well.

The pointer C is not necessarily required to be moved in the operation input. For example, the setting position of the extraction region for the OCT data and the slice to be displayed may be changed by scrolling a mouse wheel.

Figure 13:
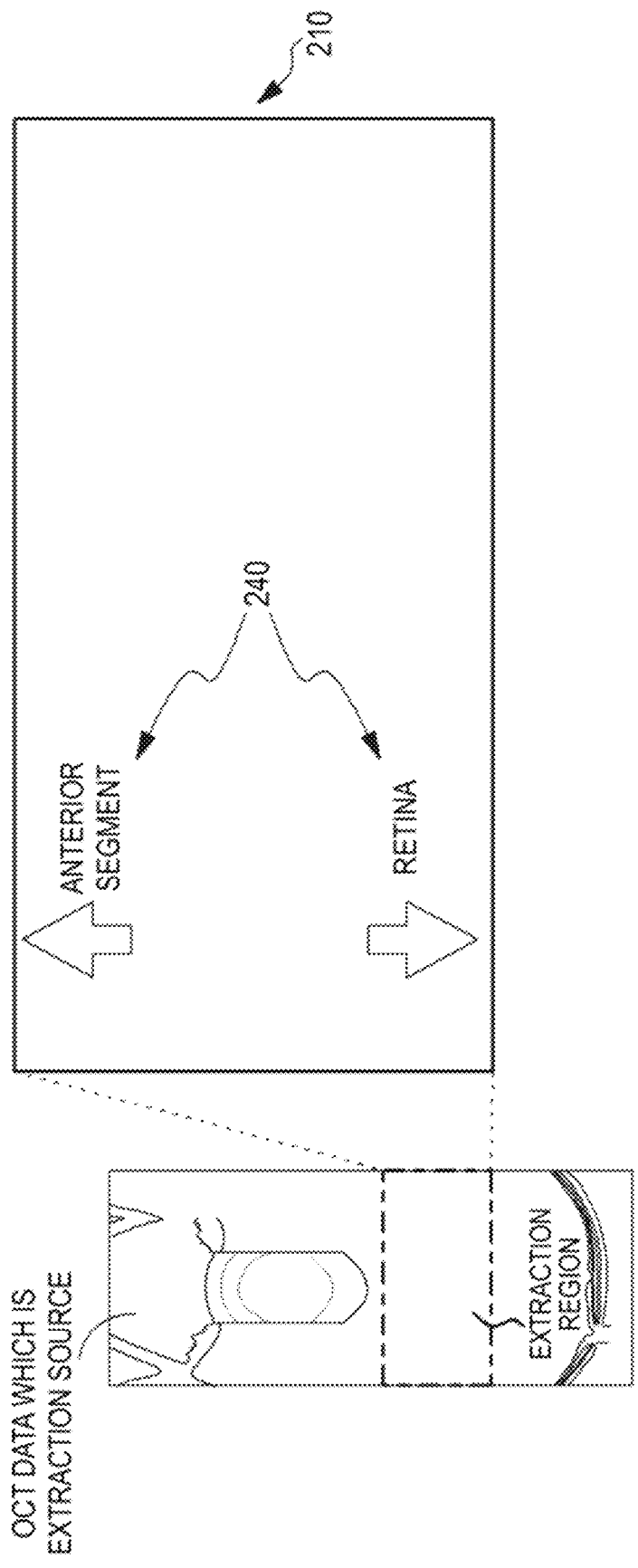
FIG. 13 is a diagram showing a display form of an extracted OCT data according to a modification example.

In the above example, the position relationship of the extraction region for the OCT data which is the extraction source is shown through the thumbnail of the OCT data which is the extraction source (image displayed in the second display region 220). However, the present disclosure is not limited thereto. The position relationship of the extraction region for the OCT data which is the extraction source may be shown on the screen without using the thumbnail. As an example, as shown in FIG. 13, the position relationship of the extraction region for the OCT data which is the extraction source may be indicated by a graphic 240 displayed in the first display region 210. In FIG. 13, in a case where the OCT data which is the extraction source includes the images of the anterior segment and the fundus, the extraction region is set between the anterior segment and the fundus. In this case, an arrow and a text shown by graphic 240 indicate the tissue of the extraction region in the vertical direction. In this case, the examiner can grasp the position of the extraction region even though the image of the tissue is not included in the extraction region. As a result, the examiner can easily adjust the position of the extraction region such that a desired tissue is displayed in the first display region 210.

In the present example, the ophthalmologic imaging apparatus for imaging the OCT data of the eye E to be examined has been described as an example, but the present disclosure is not limited thereto. For example, the present embodiment may be applied to an apparatus for imaging OCT data of an object to be examined. For example, the object to be examined may be a living body such as an eye, skin, a blood vessel, or a sample other than the living body such as a resin body.

The present disclosure includes at least aspects described in <Ophthalmologic Image Processing Methods A1 to A13>, <OCT Apparatuses B1 and B2>, <OCT Apparatuses D1 to D8>, and <OCT Apparatuses E1 to E6>. A component in each aspect can be introduced as appropriate into another aspect.

<Ophthalmologic Image Processing Methods A1 to A13, OCT Apparatuses B1 and B2>

In a case where the OCT data captured by an apparatus in the related art is displayed, the entire imaging range is displayed as it is (for example, refer to Japanese Unexamined Patent Application Publication No. 2016-55122). A range of an image of a subject in the OCT data is drawn in a relatively narrower range as the depth of penetration in the OCT data is higher (the imaging range in the depth direction is wider). Therefore, it is considered that observation of the tissue becomes difficult in a case where a display method similar to that of Japanese Unexamined Patent Application Publication No. 2016-55122 is employed.

On the contrary, the <Ophthalmologic Image Processing Methods A1 to A13> and <OCT Apparatuses B1 and B2> have been made based on at least one of the problems of the technique in the related art, and a technical issue is that at least one of acquisition and display of OCT data with high depth of penetration is performed well.

(1) Ophthalmologic Image Processing Method A1:

An ophthalmologic image processing method performed by a computer includes an acquisition step of acquiring OCT data of an eye to be examined generated by an image processor based on a spectral interference signal output from an OCT optical system that detects the spectral interference signal between measurement light guided to a tissue of the eye to be examined and reference light, a setting step of setting a depth region including an image position of the tissue as an extraction region for data on one-direction side from a zero delay position in the OCT data, and a display control step of extracting extracted OCT data corresponding to the extraction region from the OCT data and displaying the extracted OCT data in a display region set in advance on a monitor.

(2) Ophthalmologic Image Processing Method A2: in the ophthalmologic image processing method A1, in the setting step, the image position of the tissue in the OCT data is detected, and a distance between the zero delay position and at least one of an upper end and a lower end of the extraction region is adjusted based on the detected image position.

(3) Ophthalmologic Image Processing Method A3: In ophthalmologic image processing methods A1 and A2, in the display control step, information indicating a position relationship of the extraction region for the OCT data which is an extraction source is displayed on the monitor together with the extracted OCT data.

(4) Ophthalmologic Image Processing Method A4: In ophthalmologic image processing method A3, in the display control step, at least a thumbnail image of the OCT data which is the extraction source of the extracted OCT data is displayed as the information.

(5) Ophthalmologic Image Processing Method A5: In ophthalmologic image processing method A4, in the display control step, the extraction region is highlighted with respect to the thumbnail image.

(6) Ophthalmologic Image Processing Method A6: In any one of the ophthalmologic image processing methods A1 to A5, a changing step of receiving an instruction to change at least one of a depth position and a range of the extraction region for the OCT data, and changing at least one of the depth position and the range of the extraction region based on the instruction is further included, and in the display control step, in a case where at least one of the depth position and the range of the extraction region is changed based on the instruction, the extracted OCT data displayed in the display region is switched to extracted OCT data corresponding to the extraction region after the change.

(7) Ophthalmologic Image Processing Method A7: In ophthalmologic image processing method A6, in the display control step, in a case where at least one of the depth position and the range of the extraction region is changed based on the instruction, a display form of the extracted OCT data on the monitor is changed according to the extraction region after the change.

(8) Ophthalmologic Image Processing Method A8: In ophthalmologic image processing method A7, in the acquisition step, the OCT data including images of a plurality of tissues at different positions in the eye to be examined is acquired, and in the display control step, the display form is changed according to a type of the image included in the extracted OCT data.

(9) Ophthalmologic Image Processing Method A9: In any one of the ophthalmologic image processing methods A1 to A5, in the acquisition step, a plurality of the OCT data for each of a plurality of scanning lines set in advance is acquired, in the setting step, a position of the extraction region with respect to an image position of a subject is matched between the plurality of OCT data, and in the display control step, the extracted OCT data for each of the plurality of OCT data is sequentially displayed in the display region.

(10) Ophthalmologic Image Processing Method A10: In the ophthalmologic image processing method A9, in the acquisition step, each scanning line is scanned by the OCT optical system to sequentially acquire one frame of the OCT data each time the image processor generates the OCT data, in the setting step, the extraction region is set for the sequentially acquired OCT data, and in the display control step, the extracted OCT data in the sequentially acquired OCT data is displayed in the display region in real time.

(11) Ophthalmologic Image Processing Method A11: In any one of the ophthalmologic image processing methods A1 to A8, in the acquisition step, a plurality of the OCT data in which positions of the scanning lines match each other and imaging dates are different from each other is acquired, in the setting step, a position of the extraction region with respect to an image position of a subject is matched between the plurality of OCT data, and in the display control step, the extracted OCT data for each of the plurality of OCT data is sequentially displayed in the display region.

(12) Ophthalmologic Image Processing Method A11: In any one of the ophthalmologic image processing methods A1 to A11, the OCT optical system includes a wavelength sweep light source as a light source for the measurement light and the reference light.

(13) Ophthalmologic Image Processing Method A13: In the ophthalmologic image processing method A12, the wavelength sweep light source is a VCSEL wavelength sweep light source.

(14) OCT Apparatus B1:

An OCT apparatus includes an OCT optical system that detects a spectral interference signal between measurement light guided to a tissue of an eye to be examined and reference light, an image processor that generates OCT data of the eye to be examined based on the spectral interference signal output from the OCT optical system, and a computer that executes any one of the ophthalmologic image processing methods A1 to A13.

(15) OCT Apparatus B2: In the OCT apparatus B1, the OCT optical system acquires wide-area OCT data in a depth direction, and the image processor acquires the wide-area OCT data about the eye to be examined based on the spectral interference signal, the OCT apparatus further includes an optical path length difference adjusting unit that changes an optical path length difference between the measurement light and the reference light in order to adjust a depth position from which the OCT data is acquired, and a control unit that executes adjustment processing of performing at least the adjustment of the depth position and capture processing of capturing the OCT data, the control unit executes the capture processing regardless of a position of a fundus image in a case where the fundus image is located in data on one-direction side from a zero delay position in the OCT data when the depth position in the adjustment processing is an initial position.

<OCT Apparatuses C1 to C8>

In a case where the fundus is imaged by OCT, it is necessary to adjust the optical path length difference between the measurement light and the reference light according to the eye axial length of the eye to be examined. For example, in Japanese Patent Publication No. 2010-12111, when the OCT data is captured, the optical path length difference is roughly adjusted as follows. That is, a predetermined evaluation value is acquired based on the OCT data acquired in each optical path length difference while changing the optical path length difference, and the optical path length difference is adjusted to a value that maximizes the evaluation value. Thereafter, fine adjustment of the optical path length difference is further performed. The subject is required to continuously open the eyelid while adjusting the optical path length difference. Therefore, a burden is imposed on the subject according to a time required for the adjustment.

On the contrary, the <OCT Apparatuses C1 to C8> has been made based on at least one of the problems of the technique in the related art, and a technical issue is to provide the OCT apparatuses that reduce the burden on the subject due to the adjustment of the optical path length difference.

(1) OCT Apparatus C1:

An OCT apparatus includes an OCT optical system that detects a spectral interference signal between measurement light guided to a tissue of an eye to be examined and reference light and that is capable of acquiring wide-area OCT data in a depth direction, an image processor that acquires the wide-area OCT data for the eye to be examined based on the spectral interference signal output from the OCT optical system, an optical path length difference adjusting unit that changes an optical path length difference between the measurement light and the reference light in order to adjust a depth position from which the OCT data is acquired, and a control unit that executes adjustment processing of performing at least the adjustment of the depth position and capture processing of capturing the OCT data, by the control unit, a position is set such that the position from a first fundus position which is a fundus position assumed in an eye with short eye axial length or an eye with long eye axial length to a second fundus position which is a fundus position assumed in an eye with average eye axial length is included in a predetermined section in the OCT data, as an initial position of the depth position in the adjustment processing, and the capture processing is executed regardless of a position of a fundus image in a case where the fundus image is located within the predetermined section when the depth position is the initial position.

(2) OCT Apparatus C2: In the OCT apparatus C1, in the adjustment processing, in a case where the depth position is the initial position, the depth position is changed from the initial position when the fundus image is not included in the predetermined section.

(3) OCT Apparatus C3: In the OCT apparatus C2,
the other of one that is assumed to be the first fundus position among the fundus position assumed in the eye with short eye axial length and the fundus position assumed in the eye with long eye axial length is referred to as a third fundus position, and
in the adjustment processing, in a case where the fundus image is not included in the predetermined section when the depth position is the initial position, the depth position is changed to a second position such that the third fundus position is included within the predetermined section.

(4) OCT Apparatus C4: In the OCT apparatus C3,
an overlap amount of the predetermined section between when the depth position is the initial position and when the depth position is the second position is equal to or less than half of the predetermined section.

(5) OCT Apparatus C5: In the OCT apparatus C1 or C2,
in the adjustment processing,
the second fundus position is disposed in the center of the predetermined section in the initial position, and
in a case where the fundus image is not included in the predetermined section when the depth position is the initial position, the depth position is sequentially changed to a third position on the front side and a fourth position on the back side with respect to the initial position, and the capture processing is executed regardless of the position of the fundus image at a stage where the fundus image is located within the predetermined section at any one of the third position and the fourth position.

(6) OCT Apparatus C6: In any one of the OCT apparatuses C1 to C5,
the control unit further executes
setting processing of setting a depth region including the image position of the fundus as an extraction region for the OCT data acquired by the capture processing, and
display control processing of extracting extracted OCT data corresponding to the extraction region from the OCT data and displaying the extracted OCT data in a display region set in advance on a monitor.

(7) OCT Apparatus C7: In any one of the OCT apparatuses C1 to C6,
a focus adjustment unit that adjusts a focus position of the measurement light is included, and
in the adjustment processing, the control unit sets the second fundus position as an initial value of the focus position.

(8) OCT Apparatus C8: In any one of the OCT apparatuses C1 to C7,
the OCT optical system is an SS-OCT optical system.

(9) OCT Apparatus C9: In any one of the OCT apparatuses C1 to C8,
a full-ranging technique of removing a virtual image is applied to the OCT data.

<OCT Apparatuses D1 to D8>

The reciprocal of a sweep time is referred to as the sweep frequency (or sweep speed). There is an apparatus capable of adjusting the sweep frequency in the wavelength sweep light source.

When the sweep frequency is changed, a plurality of conditions in the OCT data may be changed according to the sweep frequency. On the contrary, the inventor of the present application has studied a method of maintaining other conditions while changing some of desired conditions when the sweep frequency is changed.

On the contrary, the <OCT apparatuses D1 to D8> has been made based on at least one of the problems of the technique in the related art, and a technical issue is to provide an OCT apparatus capable of acquiring good OCT data at different sweep frequencies.

(1) OCT Apparatus D1:
An OCT apparatus includes an OCT optical system including a light source that periodically sweeps a wavelength of emitted light, a light splitter that splits the light from the light source into measurement light and reference light, and a detector that detects a spectral interference signal between the measurement light guided to a tissue of an eye to be examined and the reference light,
a conversion unit that samples the spectral interference signal output from the detector and converts an analog signal into a digital signal,
an image processor that acquires OCT data of the eye to be examined by arithmetic processing on the spectral interference signal converted into the digital signal, and
an arithmetic control unit that changes a sweep frequency in the light source between at least a first value and a second value smaller than the first value and performs correction processing of correcting at least one of the control of the OCT optical system and the arithmetic processing according to the sweep frequency so as to suppress some of a plurality of conditions in the OCT data that may change with the sweep frequency.

(2) OCT Apparatus D2: In the OCT apparatus D1,
the correction processing changes a sampling rate or thins out or interpolates the spectral interference signal obtained by the sampling either before or after the analog-to-digital conversion such that the number of samplings per A scan is equal between when the sweep frequency is the first value and when the sweep frequency is the second value.

(3) OCT Apparatus D3: In the OCT apparatus D1 or D2,
mapping information for mapping the signal obtained by each sampling into a wavelength space is changed according to the sweep frequency.

(4) OCT Apparatus D3: In any one of the OCT apparatuses D1 to D3,
a light amount of the light source is changed according to the sweep frequency.

(5) OCT Apparatus D5: In the OCT apparatus D4,
an input receiving unit that receives an operation input for selecting the sweep frequency in the light source from an examiner is included.

(6) OCT Apparatus D6: In the OCT apparatus D5,
the operation input is an operation input for setting any one of a measurement site, a measurement range, and a scan pattern.

(7) OCT Apparatus D7: In any one of the OCT apparatuses D1 to D6,
a detection unit that detects opacity of a translucent body in the eye to be examined is included, and
the arithmetic control unit changes the sweep frequency in the light source according to a degree of the detected opacity.

(8) OCT Apparatus D8: In any one of the OCT apparatuses D1 to D7,
the tissue of the eye to be examined is a fundus tissue,
a detection unit that acquires a fundus image of the eye to be examined and detects image quality of the acquired image is included, and
the arithmetic control unit changes the sweep frequency in the light source according to a degree of the detected image quality.

<OCT Apparatuses E1 to E6>

When the imaging range in the depth direction is further widened, a difference in a degree of influence of the artifact due to analysis failure at each depth position becomes more noticeable in the OCT data.

On the contrary, the <OCT apparatuses E1 to E6> has been made based on the problems of the technique in the related art, and a technical issue is to obtain OCT data in which the influence of the artifact due to the analysis failure is appropriately suppressed according to the depth position.

(1) OCT Apparatus E1:

An OCT apparatus includes an OCT optical system including an OCT light source, a light splitter that splits the light from the OCT light source into measurement light and reference light, and a detector that detects a spectral interference signal between the measurement light guided to a tissue of an eye to be examined and the reference light, and an image processor that executes arithmetic processing including a Fourier analysis on a spectral interference signal acquired based on an output signal from the detector to acquire OCT data of the eye to be examined, in which preprocessing of increasing a data density as preprocessing for the arithmetic processing is executed by the image processor, and an increase amount of the data density in the preprocessing can be changed.

(2) OCT Apparatus E2: In the OCT apparatus E1, a control unit that sets the increase amount according to a depth position of a specific region in the OCT data is included.

(3) OCT Apparatus E3: In the OCT apparatus E2, the control unit can change a region to be displayed in the OCT data in a depth direction and sets the increase amount with the region to be displayed as the specific region.

(4) OCT Apparatus E4: In the OCT apparatus E2 or E3, the control unit sets the increase amount with a region in which an image of the tissue is drawn in the OCT data as the specific region.

(5) OCT Apparatus E5: In any one of the OCT apparatuses E2 to E4, the control unit sets a larger increase amount as the depth position of the specific region is farther from a zero delay position in the OCT data.

(6) OCT Apparatus E6: In any one of the OCT apparatuses E2 to E5, the control unit feeds back the increase amount corresponding to the specific region to the arithmetic processing based on the specific region in at least any one of the plurality of OCT data while a real-time display is executed in which a plurality of OCT data is sequentially acquired and displayed each time.

What is claimed is:

1. An ophthalmologic image processing method performed by a computer, the method comprising:

an acquisition step of acquiring OCT data of an eye to be examined generated by an image processor based on a spectral interference signal output from an OCT optical system, the OCT optical system detecting the spectral interference signal between measurement light guided to a tissue of the eye to be examined and reference light;

a setting step of setting a depth region including an image position of the tissue as an extraction region for data on one-direction side from a zero delay position in the OCT data; and a display control step of extracting extracted OCT data corresponding to the extraction region from the OCT data and displaying the extracted OCT data in a display region set in advance on a monitor.

2. The ophthalmologic image processing method according to claim 1, wherein, in the setting step, the image position of the tissue in the OCT data is detected, and a distance between the zero delay position and at least one of an upper end and a lower end of the extraction region is adjusted based on the detected image position.

3. The ophthalmologic image processing method according to claim 1, wherein, in the display control step, information indicating a position relationship of the extraction region for the OCT data which is an extraction source is displayed on the monitor together with the extracted OCT data.

4. The ophthalmologic image processing method according to claim 3, wherein, in the display control step, at least a thumbnail image of the OCT data which is the extraction source of the extracted OCT data is displayed as the information.

5. The ophthalmologic image processing method according to claim 4, wherein, in the display control step, the extraction region is highlighted with respect to the thumbnail image.

6. The ophthalmologic image processing method according to claim 1, further comprising:

a changing step of receiving an instruction to change at least one of a depth position and a range of the extraction region for the OCT data, and changing at least one of the depth position and the range of the extraction region based on the instruction, wherein, in the display control step, in a case where at least one oldie depth position and the range of the extraction region is changed based on the instruction, the extracted OCT data displayed in the display region is switched to extracted OCT data corresponding to the extraction region after the change.

7. The ophthalmologic image processing method according to claim 6, wherein, in the display control step, in a case where at least one of the depth position and the range of the extraction region is changed based on the instruction, a display form of the extracted OCT data on the monitor is changed according to the extraction region after the change.

8. The ophthalmologic image processing method according to claim 7, wherein, in the acquisition step, the OCT data including images of a plurality of tissues at different positions in the eye to be examined is acquired, and in the display control step, the display form is changed according to a type of the image included in the extracted OCT data.

9. The ophthalmologic image processing method according to claim 1, wherein, in the acquisition step, a plurality of the OCT data for each of a plurality of scanning lines set in advance is acquired, in the setting step, a position of the extraction region with respect to an image position of a subject is matched between the plurality of OCT data, and in the display control step, the extracted OCT data for each of the plurality of OCT data is sequentially displayed in the display region.

10. The ophthalmologic image processing method according to claim 9,
wherein, in the acquisition step, each scanning line is scanned by the OCT optical system to sequentially acquire one frame of the OCT data each time the image processor generates the OCT data,
in the setting step, the extraction region is set for the sequentially acquired OCT data, and
in the display control step, the extracted OCT data in the sequentially acquired OCT data is displayed in the display region in real time.

11. The ophthalmologic image processing method according to claim 1,
wherein, in the acquisition step, a plurality of the OCT data in which positions of the scanning lines match each other and imaging dates are different from each other is acquired,
in the setting step, a position of the extraction region with respect to an image position of a subject is matched between the plurality of OCT data, and
in the display control step, the extracted OCT data for each of the plurality of OCT data is sequentially displayed in the display region.

12. The ophthalmologic image processing method according to claim 1,
wherein the OCT optical system includes a wavelength sweep light source as a light source for the measurement light and the reference light.

13. The ophthalmologic image processing method according to claim 12,
wherein the wavelength sweep light source is a VCSEL wavelength sweep light source.

14. An OCT apparatus comprising:
an OCT optical system that detects a spectral interference signal between measurement light guided to a tissue of an eye to be examined and reference light;
an image processor that generates OCT data of the eye to be examined based on the spectral interference signal output from the OCT optical system; and
a computer that executes the ophthalmologic image processing method according to claim 1.

15. The OCT apparatus according to claim 14,
wherein the OCT optical system acquires wide-area OCT data in a depth direction,
wherein the image processor acquires the wide-area OCT data about the eye to be examined based on the spectral interference signal,
wherein the OCT apparatus further comprising:
an optical path length difference adjusting unit that changes an optical path length difference between the measurement light and the reference light in order to adjust a depth position from which the OCT data is acquired; and
a control unit that executes adjustment processing of performing at least the adjustment of the depth position and capture processing of capturing the OCT data, and
wherein the control unit executes the capture processing regardless of a position of a fundus image in a case where the fundus image is located in data on one-direction side from a zero delay position in the OCT data when the depth position in the adjustment processing is an initial position.

* * * * *